United States Patent
Tiecke et al.

(10) Patent No.: US 9,749,044 B1
(45) Date of Patent: Aug. 29, 2017

(54) LUMINESCENT DETECTOR FOR FREE-SPACE OPTICAL COMMUNICATION

(71) Applicant: Facebook, Inc., Menlo Park, CA (US)

(72) Inventors: Tobias Gerard Tiecke, Menlo Park, CA (US); Kevin Jerome Quirk, Los Altos, CA (US); Thibault Michel Max Peyronel, San Francisco, CA (US); Shih-Cheng Wang, Cupertino, CA (US)

(73) Assignee: Facebook, Inc., Menlo Park, CA (US)

( * ) Notice: Subject to any disclaimer, the term of this patent is extended or adjusted under 35 U.S.C. 154(b) by 0 days.

(21) Appl. No.: 15/090,786

(22) Filed: Apr. 5, 2016

(51) Int. Cl.
*H04B 10/00* (2013.01)
*H04B 10/11* (2013.01)
*H04B 10/25* (2013.01)
*H04B 10/66* (2013.01)
*G01N 21/64* (2006.01)

(52) U.S. Cl.
CPC ............ *H04B 10/11* (2013.01); *G01N 21/64* (2013.01); *H04B 10/25* (2013.01); *H04B 10/66* (2013.01); *G01N 2021/6497* (2013.01)

(58) Field of Classification Search
USPC ...................................................... 398/1–214
See application file for complete search history.

(56) References Cited

U.S. PATENT DOCUMENTS

| | | | | |
|---|---|---|---|---|
| 4,081,672 A | * | 3/1978 | Caspers .................... | G02B 6/02 250/227.24 |
| 4,110,123 A | * | 8/1978 | Goetzberger ......... | H01L 31/055 136/247 |
| 4,149,902 A | * | 4/1979 | Mauer .................... | H01L 31/055 126/648 |
| 4,175,982 A | * | 11/1979 | Loutfy ................ | H01L 51/0078 136/255 |
| 4,262,206 A | * | 4/1981 | Viehmann ......... | H01L 31/02322 136/247 |
| 4,329,535 A | * | 5/1982 | Rapp ..................... | H01L 31/055 136/247 |
| 4,357,486 A | * | 11/1982 | Blieden ................. | H01L 31/055 136/247 |
| 4,367,367 A | * | 1/1983 | Reisfeld .................... | C03C 3/16 136/247 |
| 4,371,897 A | * | 2/1983 | Kramer ................ | H04N 1/0281 250/227.31 |
| 4,467,208 A | * | 8/1984 | Muller ..................... | G01J 1/58 136/247 |

(Continued)

*Primary Examiner* — Agustin Bello
(74) *Attorney, Agent, or Firm* — Baker Botts L.L.P.

(57) ABSTRACT

In one embodiment, an apparatus includes a wavelength-shifting element configured to receive an input-light signal. The wavelength-shifting element includes a wavelength-shifting material configured to absorb at least a portion of the received input-light signal and produce an emitted-light signal from the absorbed portion of the received input-light signal. The apparatus also includes an optical-concentrating element configured to receive at least a portion of the emitted-light signal and concentrate the received portion of the emitted-light signal onto a photodetector. The apparatus further includes the photodetector configured to receive the concentrated portion of the emitted-light signal and produce an electrical current corresponding to the concentrated portion of the emitted-light signal.

20 Claims, 8 Drawing Sheets

(56) References Cited

U.S. PATENT DOCUMENTS

| | | | | |
|---|---|---|---|---|
| 4,629,821 A * | 12/1986 | Bronstein-Bonte | C09K 11/06 | 136/247 |
| 4,764,984 A * | 8/1988 | Franke | G01J 1/58 | 250/361 R |
| 5,449,413 A * | 9/1995 | Beauchamp | C03C 4/0085 | 136/256 |
| 5,568,304 A * | 10/1996 | Baur | G02B 5/22 | 250/361 R |
| 5,816,238 A * | 10/1998 | Burns | C08K 5/0041 | 126/569 |
| 6,211,524 B1 * | 4/2001 | Vardeny | G01J 1/58 | 250/458.1 |
| 6,538,191 B1 * | 3/2003 | MacDonald | H01L 31/02322 | 136/247 |
| 6,744,960 B2 * | 6/2004 | Pelka | B82Y 10/00 | 362/259 |
| 6,784,603 B2 * | 8/2004 | Pelka | B82Y 10/00 | 313/110 |
| 6,819,845 B2 * | 11/2004 | Lee | B82Y 10/00 | 257/E21.09 |
| 7,333,705 B2 * | 2/2008 | Hyde | B82Y 20/00 | 385/122 |
| 7,499,619 B2 * | 3/2009 | Hyde | B82Y 20/00 | 385/122 |
| 7,541,537 B2 * | 6/2009 | Madigan | H01L 31/02168 | 136/246 |
| 7,787,734 B2 * | 8/2010 | Hyde | B82Y 20/00 | 385/129 |
| 7,872,442 B2 * | 1/2011 | Liang | H02J 7/0044 | 136/206 |
| 8,022,292 B2 * | 9/2011 | Arianpour | H01L 31/02168 | 136/261 |
| 9,123,846 B2 * | 9/2015 | Le Perchec | H01L 31/055 | |
| 2008/0048936 A1 * | 2/2008 | Powell | G02B 3/0056 | 345/55 |
| 2009/0129726 A1 * | 5/2009 | Hyde | B82Y 20/00 | 385/18 |
| 2010/0046234 A1 * | 2/2010 | Abu-Ageel | G02B 3/0006 | 362/308 |
| 2014/0137941 A1 * | 5/2014 | Orsley | A01G 9/02 | 136/259 |
| 2014/0204449 A1 * | 7/2014 | McCarthy | G02B 5/223 | 359/288 |
| 2015/0244457 A1 * | 8/2015 | O'Brien | G06F 1/1698 | 398/118 |
| 2015/0304027 A1 * | 10/2015 | Nciri | G01J 3/10 | 398/119 |
| 2016/0042676 A1 * | 2/2016 | Berkeley | G09G 3/006 | 345/589 |

* cited by examiner

LUMINESCENT DETECTOR FOR FREE-SPACE OPTICAL COMMUNICATION

TECHNICAL FIELD

This disclosure generally relates to free-space optical communication.

BACKGROUND

A communication system may include an optical-communication link where an optical transmitter and an optical receiver send or receive data using free-space optical communication. An optical-communication link may be a one-way link where one communication station transmits information to another communication station, or a communication link may be bidirectional where both communication stations transmit and receive information. An optical-communication link may have a data rate between 1 megabit per second and 100 gigabits per second. For example, a free-space optical-communication link may have a data rate of 10 gigabits per second. In a free-space optical-communication link, an optical transmitter and an optical receiver may be separated by relatively short distances (e.g., 1 m to 1 km) or moderate to long distances (e.g., 1 km to 36,000 km).

An optical transmitter and receiver may communicate using any suitable optical wavelength, such as for example, 405 nm, 780 nm, 1.3 µm, or 1.5 µm. An optical transmitter may transmit an optical signal by applying a current modulation to a laser diode or a light-emitting diode. An optical receiver may include a photodetector that converts received light from the transmitter into an electrical current. An optical receiver may also include a transimpedance amplifier that produces an output voltage signal based on the electrical current from the photodetector.

SUMMARY OF PARTICULAR EMBODIMENTS

In particular embodiments, a luminescent detector may be configured to receive an input optical signal, produce wavelength-shifted light from the input optical signal, and then produce an output electrical current from the wavelength-shifted light. The input optical signal may include high-speed data modulated onto the optical signal and sent from a transmitter located some distance away from the luminescent detector (e.g., located 1 m to 36,000 km away). In particular embodiments, a luminescent detector may include a wavelength-shifting element and a photodetector. Additionally, in particular embodiments, a luminescent detector may include a concentrating element (e.g., a lens or a nonimaging optical element). The wavelength-shifting element may include a wavelength-shifting material (e.g., a fluorescent dye or quantum dots) that absorbs the input optical signal and emits light at a longer wavelength through a fluorescence process. The emitted light may be radiated substantially equally in all directions, or the emitted light may be radiated in a directional manner. As an example and not by way of limitation, the wavelength-shifting element may include a plasmonic or dielectric structure that causes the emitted light to be radiated in a directional manner primarily along the forward or backward directions. The luminescent detector may include a lens or a nonimaging optical element that receives the light radiated in the forward direction and concentrates the received light onto a photodetector. As another example and not by way of limitation, the wavelength-shifting element may include a plasmonic or dielectric structure that receives a portion of the emitted light and causes the received portion of emitted light to be concentrated as a converging beam directed onto a photodetector. The photodetector produces an electrical-current signal that corresponds to the high-speed data modulated onto the optical signal sent by the optical transmitter. The electrical-current signal may be sent to a transimpedance amplifier to produce an output-voltage signal which may be sent to other electronic devices for recovery and processing of the high-speed data.

In particular embodiments, the light emitted by the wavelength-shifting material may be substantially directional. As an example and not by way of limitation, even if the input optical signal received by the luminescent detector has a distorted, nonuniform, or time-varying distribution of incidence angles (which may be caused at least in part by atmospheric turbulence experienced as the optical signal propagates from the transmitter to the luminescent detector), the emitted light from the wavelength-shifting element may have a substantially directional character, hence a small numerical aperture. A luminescent detector may offer a relatively large effective detector area, a relatively fast response time, and a relatively large field of view. Therefore, a luminescent detector may be substantially insensitive to the incidence angle or phase fluctuations of the input optical signal. Since the light emitted by the wavelength-shifting material does not exhibit the large spread in propagation direction of the input optical signal, the emitted light may be concentrated to a small spot that is incident on a photodetector. Additionally, even though the distribution of incidence angles of the input light may vary in time due to atmospheric turbulence, the concentrated spot may remain incident on the photodetector, resulting in a significant reduction in amplitude fluctuations of the electrical-current signal produced by the photodetector. Moreover, the large effective detector area, the large field of view, and the relative insensitivity to incidence angle provided by a luminescent detector may allow the beam-pointing accuracy and tracking requirements for the optical transmitter to be relaxed.

The embodiments disclosed above are only examples, and the scope of this disclosure is not limited to them. Particular embodiments may include all, some, or none of the components, elements, features, functions, operations, or steps of the embodiments disclosed above. Embodiments according to the invention are in particular disclosed in the attached claims directed to a method, a storage medium, a system and a computer program product, wherein any feature mentioned in one claim category, e.g. method, can be claimed in another claim category, e.g. system, as well. The dependencies or references back in the attached claims are chosen for formal reasons only. However any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

DESCRIPTION OF EXAMPLE EMBODIMENTS

Figure 1:
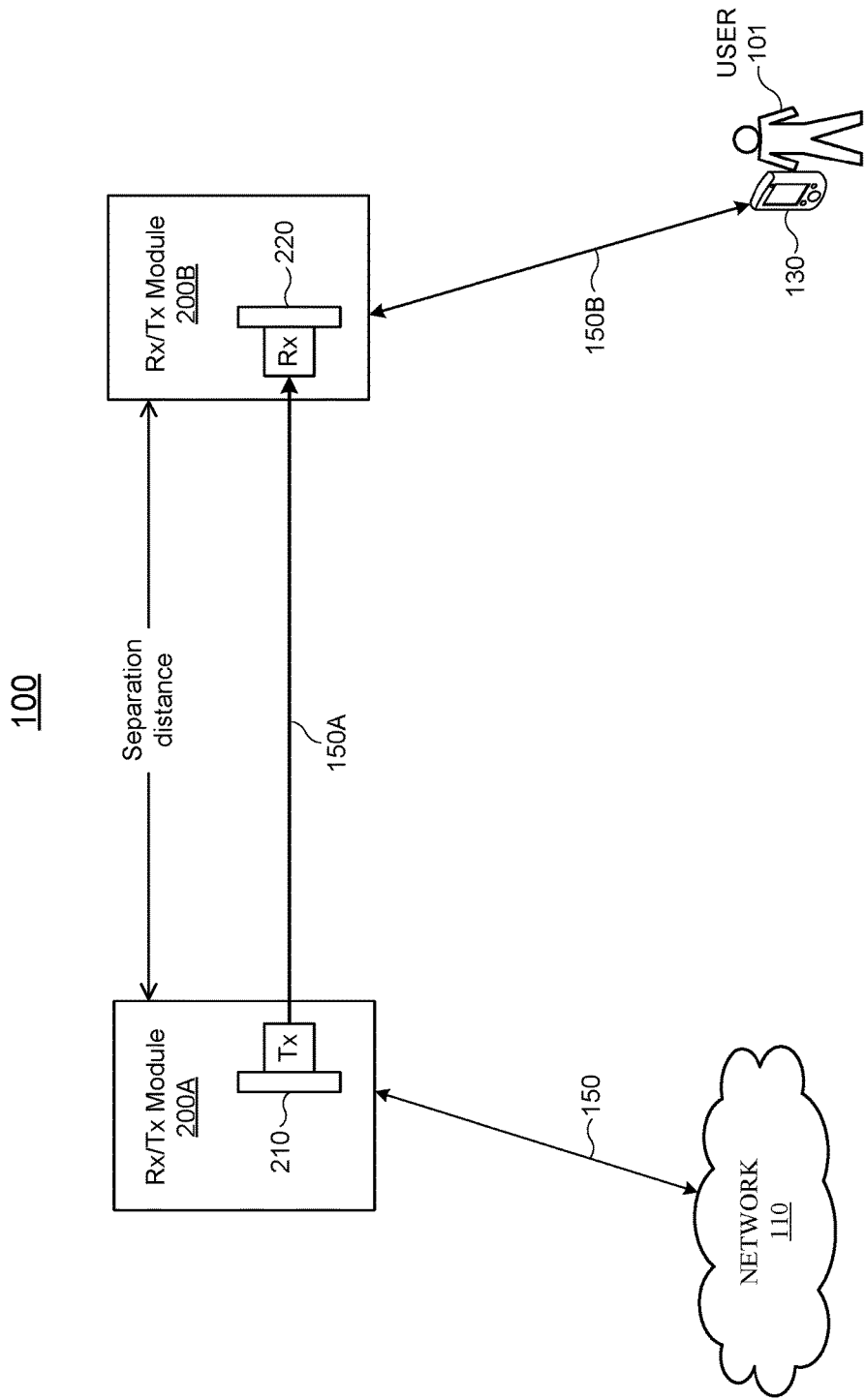
FIG. 1 illustrates an example network environment that includes a pair of Rx/Tx modules connected by a free-space optical link.

FIG. 1 illustrates an example network environment 100 that includes a pair of Rx/Tx modules (200A and 200B) connected by a free-space optical link 150A. In particular embodiments, Rx/Tx module 200A or 200B may be referred to as a receive/transmit module, a receiver/transmitter module, a receiver module, a transmitter module, or a transceiver module. As illustrated in FIG. 1, Rx/Tx module 200A includes optical transmitter 210, and Rx/Tx module 200B includes optical receiver 220. Link 150A may be a one-way free-space optical (FSO) link where transmitter 210 of Rx/Tx module 200A transmits data in the form of a modulated optical signal to receiver 220 of Rx/Tx module 200B. In particular embodiments, Rx/Tx module 200A may also include an optical receiver 220 (not illustrated in FIG. 1), and Rx/Tx module 200B may also include an optical transmitter 210 (not illustrated in FIG. 1). As an example and not by way of limitation, link 150A may be a bidirectional link where Rx/Tx modules 200A and 200B each include an optical transmitter 210 and an optical receiver 220. Modules 200A and 200B may each be configured to send and receive information using their respective transmitter 210 and receiver 220. In particular embodiments, link 150A may be referred to as a free-space optical link, a FSO link, an optical-communication link, a FSO communication link, an optical link, or a communication link.

In particular embodiments, a network environment 100 may provide wireless connectivity, through one or more links 150, to a network 110 or a client system 130. As an example and not by way of limitation, one or more links 150 may connect client system 130 to Rx/Tx module 200B, and one or more other links 150 may connect Rx/Tx module 200B to network 110. In the example of FIG. 1, client system 130 is connected to Rx/Tx module 200B by link 150B, which may be a wireline, wireless, or optical (e.g., fiber-optic or free-space) link. Rx/Tx module 200B is connected to Rx/Tx module 200A by free-space optical link 150A, which may be a one-way link with a data rate of 1 to 100 gigabits per second (Gbps) or a bidirectional link with a data rate of 1 to 100 gigabits per second (Gbps) in both directions. Additionally, Rx/Tx module 200A is connected to network 110 by link 150, which may be a wireline, wireless, or optical link 150. Although FIG. 1 illustrates a particular arrangement of client system 130, links 150, Rx/Tx modules 200, and network 110, this disclosure contemplates any suitable arrangement of client system 130, links 150, Rx/Tx modules 200, and network 110. Moreover, although FIG. 1 illustrates a particular number of client systems 130, links 150, Rx/Tx modules 200, and networks 110, this disclosure contemplates any suitable number of client systems 130, links 150, Rx/Tx modules 200, and networks 110. As an example and not by way of limitation, network environment 100 may include multiple client systems 130, links 150, Rx/Tx modules 200, and networks 110.

This disclosure contemplates any suitable network 110. As an example and not by way of limitation, one or more portions of network 110 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 110 may include one or more networks 110.

This disclosure contemplates any suitable links 150. In particular embodiments, one or more links 150 include one or more wireline (such as for example Digital Subscriber Line (DSL) or Data Over Cable Service Interface Specification (DOCSIS)), wireless (such as for example RF, Wi-Fi, or Worldwide Interoperability for Microwave Access (WiMAX)), or optical (such as for example free-space optical, Gigabit Ethernet (e.g., 10 Gigabit Ethernet) over optical fiber, Synchronous Optical Network (SONET), or Synchronous Digital Hierarchy (SDH)) links. In particular embodiments, one or more links 150 each include an ad hoc network, an intranet, an extranet, a VPN, a LAN, a WLAN, a WAN, a WWAN, a MAN, a portion of the Internet, a portion of the PSTN, a cellular technology-based network, a satellite communications technology-based network, another link 150, or a combination of two or more such links 150. Links 150 need not necessarily be the same throughout network environment 100. One or more first links 150 may differ in one or more respects from one or more second links 150.

In particular embodiments, a free-space optical (FSO) link 150 or a wireless link 150 may refer to any suitable electromagnetic-radiation-based communication signal transmitted through free space. As an example and not by way of limitation, a FSO link 150 may be a free-space optical link (e.g., link 150A in FIG. 1) that uses light for sending or receiving data. A FSO link 150 may use light having any suitable wavelength, such as for example, near-ultraviolet light (e.g., light with a wavelength between approximately 100 nm and 400 nm), visible light (e.g., light with a wavelength between approximately 400 nm and 750 nm), or near-infrared light (e.g., light with a wavelength between approximately 750 nm and 2.5 µm). As another example and not by way of limitation, a wireless link 150 may use radio-frequency (RF) signals for communication (e.g., link 150B in FIG. 1). A wireless RF link 150 may operate at any suitable frequency from approximately 300 kHz to approximately 300 GHz. In particular embodiments, the unit of length "µm" may be referred to as a micrometer or a micron (e.g., 1 µm equals $10^{-6}$ meters). Although this disclosure describes and illustrates particular FSO or wireless links having particular wavelengths or frequencies, this disclosure contemplates any suitable FSO or wireless links having any suitable wavelengths or frequencies.

In particular embodiments, two Rx/Tx modules (e.g., Rx/Tx modules 200A and 200B in FIG. 1) may be directly connected to one another by a point-to-point wireless communications link 150. In particular embodiments, a point-to-point link 150 may refer to a communications link 150 that directly and exclusively connects two Rx/Tx modules to one another. In particular embodiments, a point-to-point communications link 150 may be a one-way link 150 (e.g., information or signals are sent in one direction from a transmitter 210 to a receiver 220) or a bidirectional link 150 (e.g., data is sent in both directions between two Rx/Tx modules). As an example and not by way of limitation, a bidirectional point-to-point link 150 between two Rx/Tx modules (e.g., Rx/Tx modules 200A and 200B in FIG. 1) may provide a data rate of 1-100 Gbps in each direction. In particular embodiments one or more Rx/Tx modules may be connected to one or more other Rx/Tx modules by a multi-point link 150. As an example and not by way of limitation, one transmitter 210 may broadcast an optical signal that may be received by two or more receivers 220. As another example and not by way of limitation, one receiver 220 may receive two or more optical signals sent by two or more respective transmitters 210.

In particular embodiments, a user 101 may access network 110 on a client system 130 through one or more links 150. As illustrated in FIG. 1, client system 130 may connect to network 110 via links 150, 150A, and 150B. In particular embodiments, user 101 may be an individual (human user), an entity (e.g., an enterprise, business, or third-party application), or a group (e.g., of individuals or entities) that interacts or communicates, at least in part, by a link 150 provided by a Rx/Tx module 200A or 200B. Client system 130 may be any suitable computing device, such as, for example, a personal computer, a laptop computer, a cellular telephone, a smartphone, a tablet computer, or an augmented/virtual reality device. This disclosure contemplates any suitable client systems 130. A client system 130 may enable a network user at client system 130 to access network 110. A client system 130 may enable its user 101 to communicate with other users at other client systems 130. Although this disclosure describes and illustrates particular client systems accessing particular networks via particular links, this disclosure contemplates any suitable client systems accessing any suitable networks via any suitable links.

In particular embodiments, an Rx/Tx module 200 may be located on the ground (e.g., in a ground-based communication station) or may be airborne (e.g., in an unmanned aerial vehicle). As an example and not by way of limitation, transmitter 210 and receiver 220 may each be located within the same room or building and may be located approximately 1 to 50 meters apart (e.g., separation distance illustrated in FIG. 1 may be 1-50 meters). As another example and not by way of limitation, transmitter 210 and receiver 220 may be used for building-to-building communication and may be located approximately 50 meters to 1 km apart. As another example and not by way of limitation, transmitter 210 and receiver 220 may each be part of a ground-based communication station, and the two ground-based communication stations may have a separation distance of approximately 1 km to 100 km. As another example and not by way of limitation, transmitter 210 may be part of a ground-based communication station, and receiver 220 may be located in an unmanned aerial vehicle (UAV). The UAV (which may be referred to as a drone, remotely piloted aircraft, or autonomous aircraft) may be configured to fly at a cruising altitude within a range of approximately 3,000 feet to approximately 100,000 feet above sea level. The UAV may be connected to the Internet via optical link 150A, and the UAV may provide wireless connectivity to the Internet for one or more client systems 130 located in a terrestrial area below the UAV. As another example and not by way of limitation, receiver 220 may be located in a satellite operating in a low Earth orbit (LEO), medium Earth orbit (MEO), or a geostationary orbit (GEO). For example, receiver 220 may be located in a GEO satellite with an altitude of approximately 35,800 km above mean sea level. Although this disclosure describes and illustrates particular transmitters and receivers having particular locations and particular separation distances, this disclosure contemplates any suitable transmitters and receivers having any suitable locations and any suitable separation distances.

In particular embodiments, transmitter 210 and receiver 220 may each be stationary or moving. As an example and not by way of limitation, transmitter 210 and receiver 220 may each be stationary (e.g., located on or attached to a stationary object, such as for example, a table, floor, wall, ceiling, building, or tower) where the location or orientation of the transmitter 210 does not change significantly with respect to the receiver 220. In particular embodiments, transmitter 210 may be stationary, and receiver 220 may be moving with respect to the transmitter 210. As an example and not by way of limitation, transmitter 210 may be located in a non-moving ground station, and receiver 220 may be located in a UAV flying along a flight path at an altitude of approximately 60,000 to 70,000 feet above the transmitter 210. As another example and not by way of limitation, receiver 220 may be coupled to a head-mounted display (HIVID) for an augmented/virtual reality device. A user 101 wearing the HIVID may be able to move with respect to a transmitter 210 that sends an optical signal to the receiver 220. In particular embodiments, receiver 220 may be part of client system 130. As an example and not by way of limitation, client system 130 may be an augmented/virtual reality device (e.g., an HIVID worn by user 101) with receiver 220 integrated into the augmented/virtual reality device, and link 150B may include one or more wires, printed-circuit-board traces, or coaxial cables connecting receiver 220 to a chip within client system 130 that performs data recovery.

In particular embodiments, a FSO link 150 between a transmitter 210 and a receiver 220 may be a one-way link or a bidirectional link and may have any suitable data rate. As an example and not by way of limitation, FSO link 150A illustrated in FIG. 1 may have a data rate of approximately 1 megabit per second (Mbps) to 100 gigabits per second (Gbps). As another example and not by way of limitation, link 150A may be a one-way link with a data rate of 1 Gbps, 2.4 Gbps, or 10 Gbps. As another example and not by way of limitation, link 150A may be a bidirectional link with a data rate of 32 Gbps in each direction. In particular embodiments, a bidirectional link 150 may be an asymmetric link (e.g., a bidirectional link having different data rates in each direction) or a hybrid link (e.g., a bidirectional link using different communication formats in each direction). As an example and not by way of limitation, an asymmetric link 150 between a HMD and a console (e.g., a computer that broadcasts high-definition video content to the HIVID) may have a relatively high data rate (e.g., 1 Gbps or higher) for the console-to-HIVID portion of the link and a lower data rate (e.g., approximately 1 Mbps) for the HIVID-to-console portion of the link. As another example and not by way of limitation, a hybrid link 150 between a HIVID and a console may use a FSO communication technique for the console-to-HIVID portion of the link and an RF wireless technique (e.g., Wi-Fi) for the HIVID-to-console portion of the link. Although this disclosure describes and illustrates particular communication links having particular data rates and particular formats, this disclosure contemplates any suitable communication links having any suitable data rates and any suitable formats.

In particular embodiments, optical transmitter 210 (which may be referred to as a transmitter or a laser transmitter) may include various optical, opto-electronic, or electronic components, such as for example, a laser source, a light-emitting diode (LED), a lens, an aiming mechanism, or a mirror. As an example and not by way of limitation, a laser source in transmitter 210 may include an indium-gallium-nitride (InGaN) diode laser that produces light with a peak wavelength in the range of 400-410 nm, an aluminum-gallium-arsenide (AlGaAs) diode laser that produces light with a peak wavelength in the range of 780-830 nm, or an indium-gallium-arsenide-phosphide (InGaAsP) diode laser that produces light with a peak wavelength in the range of 1.3-1.6 μm. As another example and not by way of limitation, transmitter 210 may include an InGaN diode laser operating at approximately 405 nm with an average optical output power of approximately 0.1 to 100 mW. The InGaN diode laser may be current modulated to produce a modulated optical signal. As another example and not by way of limitation, transmitter 210 may include a continuous-wave (CW) diode laser coupled to an external amplitude modulator (e.g., a lithium-niobate amplitude modulator). As another example and not by way of limitation, transmitter 210 may include an LED that is current modulated to produce a modulated optical signal. In particular embodiments, transmitter 210 may include a lens for collimating or adjusting the optical beam emitted by a laser source. As an example and not by way of limitation, a lens may be positioned toward or away from the laser-source output to adjust the divergence angle, collimation, focusing, or size of the optical beam. In particular embodiments, transmitter 210 may include a pointing and tracking mechanism for adjusting the pointing or aiming of the optical beam. As an example and not by way of limitation, a mechanical tip-tilt assembly may be used to adjust the orientation of the transmitter 210 allowing the pointing of the emitted laser beam to be changed. As another example and not by way of limitation, the optical beam may be configured to reflect off a beam-steering mirror, and the orientation of the mirror may be adjusted to change the pointing of the optical beam. Although this disclosure describes and illustrates particular optical transmitters that include particular components, this disclosure contemplates any suitable optical transmitters that include any suitable components.

Figure 2:
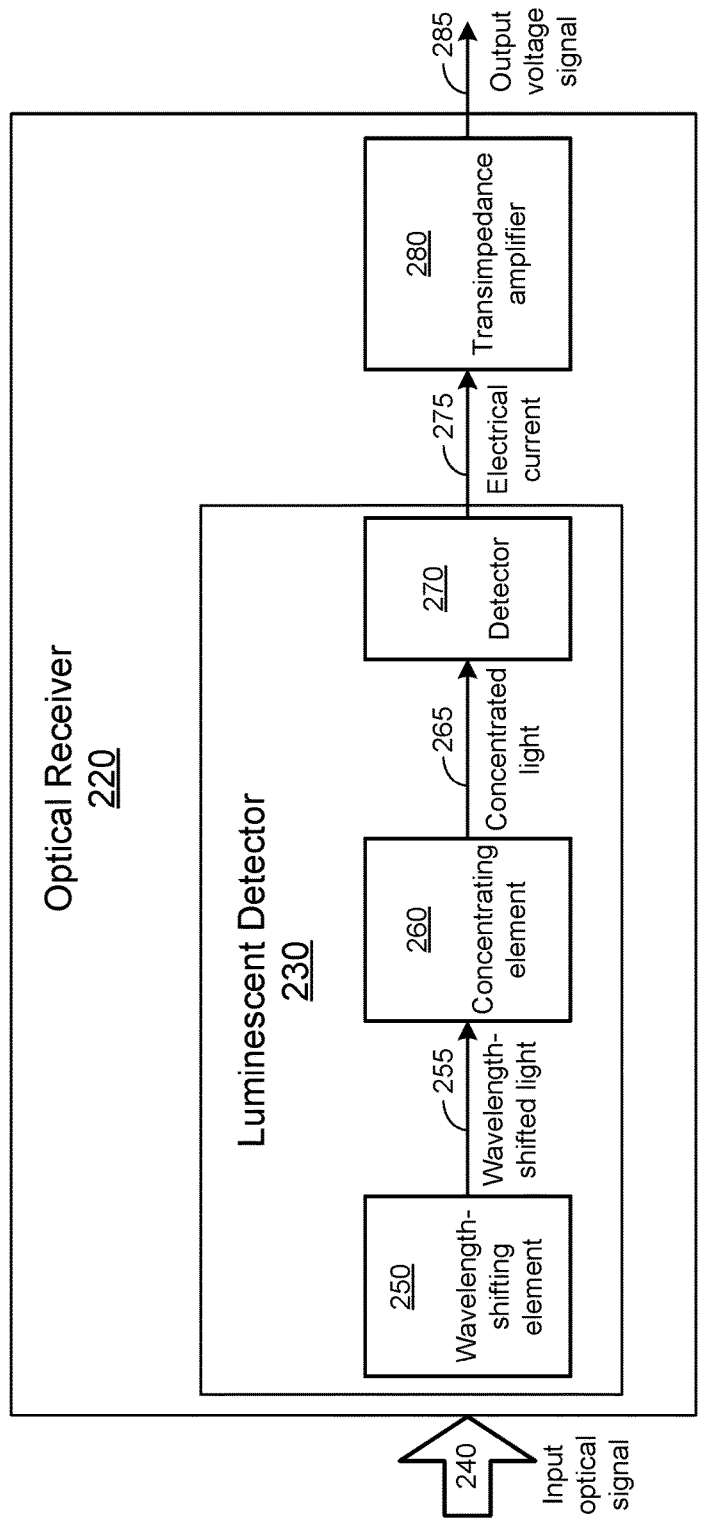
FIG. 2 illustrates a block diagram of an example optical receiver.

FIG. 2 illustrates a block diagram of an example optical receiver 220. In particular embodiments, optical receiver 220 may receive an input optical signal 240. As an example and not by way of limitation, input optical signal 240 may be a free-space optical-communication signal sent from an optical transmitter 210. In particular embodiments, an input optical signal 240 may be referred to as an input-light signal, input light, a light signal, an input-light beam, a light beam, an optical signal, an input optical beam, an input beam, an input laser beam, a laser beam, or an optical beam. The input optical signal 240 may have any suitable power, intensity, or wavelength. In particular embodiments, the input optical signal 240 may have an optical intensity at optical receiver 220 of approximately 0.01 to 100 mW/cm². As an example and not by way of limitation, input optical signal 240 may have a peak wavelength of approximately 405 nm and an optical intensity of 10 to 100 μW/cm². As another example and not by way of limitation, input optical signal 240 may have a peak wavelength of 1.4-1.6 μm and an optical intensity of 10-100 mW/cm². In particular embodiments, the input optical signal 240 may include near-ultraviolet light, visible light, or near-infrared light. As an example and not by way of limitation, the input optical signal 240 may include light having a peak wavelength of approximately 405 nm, 635 nm, 780 nm, 1 μm, 1.1 μm, 1.3 μm, or 1.5 μm. In particular embodiments, the input optical signal 240 received by the optical receiver 220 may have any suitable beam size, such as for example a beam diameter of approximately 1 mm to 20 cm. Although this disclosure describes and illustrates particular optical beams having particular intensities and particular wavelengths, this disclosure contemplates any suitable optical beams having any suitable intensities and any suitable wavelengths.

In the example of FIG. 2, optical receiver 220 includes luminescent detector (LD) 230 and transimpedance amplifier (TIA) 280. In particular embodiments, luminescent detector 230 may be configured to receive input optical signal 240 and produce electrical current 275 based on the received optical signal 240. In FIG. 2, the TIA 280 receives electrical current 275 from LD 230 and performs a transimpedance amplification of the electrical-current signal 275. In particular embodiments, a transimpedance amplification may refer to an electrical amplification process where an input electrical current 275 is converted into an output voltage 285. In FIG. 2, TIA 280 produces an output voltage signal 285 that corresponds to the input electrical-current signal 275. A transimpedance amplification may be characterized in part by a transimpedance gain (G) which has units of volts per ampere (V/A). As an example and not by way of limitation, an output voltage signal $V_{out}$ may be related to an input electrical-current signal $I_{input}$ by the expression $V_{out}=G \times I_{input}$. In particular embodiments, TIA 280 may have a transimpedance gain of approximately 100 V/A to $10^4$ V/A. As an example and not by way of limitation, TIA 280 may have a transimpedance gain of 800 V/A, and an electrical current 275 of 1 mA will result in an output voltage signal 285 of approximately 0.8 volts, based on the above expression (e.g., 800 V/A×1 mA=0.8 V).

In particular embodiments, TIA 280 may be configured to reduce, remove, or filter out a direct-current (DC) or constant-offset portion from electrical current 275. As an example and not by way of limitation, TIA 280 may have an AC-coupled (or, alternating-current-coupled) configuration or may include a high-pass filter that reduces, removes, or filters out a DC portion from the electrical-current signal 275. Removing the DC-current component may reduce or eliminate the sensitivity of TIA 280 to effects associated with ambient background light (e.g., room light or sunlight). Although this disclosure describes and illustrates particular transimpedance amplifiers having particular transimpedance gain and particular configurations, this disclosure contemplates any suitable transimpedance amplifiers having any suitable transimpedance gain and any suitable configuration.

In particular embodiments, input optical signal 240 may include high-speed data modulated onto the optical signal according to any suitable modulation scheme, such as for example, amplitude-shift keying (ASK) or wavelength-shift keying (WSK). As an example and not by way of limitation, optical signal 240 may include a 1-Gbps stream of on-off keyed (OOK) digital data produced at transmitter 210 by applying a current modulation to a laser diode. As another example and not by way of limitation, an orthogonal frequency division multiplexing (OFDM) scheme may be applied where the optical signal intensity 240 includes a superposition of sub-channels of independently modulated data. The sub-channels may be modulated using a quadrature amplitude modulation (QAM) scheme (e.g., 16-QAM, 32-QAM, 64-QAM, or 256-QAM) or a binary phase-shift keying (BPSK) scheme. As an example and not by way of limitation, approximately 100 sub-channels may be combined to produce an optical signal 240 with a data rate of 2-2.5 Gbps. In particular embodiments, the output voltage signal 285 from TIA 280 may be sent to a physical-layer chip which may perform data recovery using an analog-to-digital converter, a demodulator, or a forward-error-correction decoder.

In particular embodiments, a luminescent detector 230 may refer to an apparatus configured to receive an input-light signal 240, produce wavelength-shifted light 255 from the input-light signal 240 using a luminescent material, and produce an output electrical current 275 from the wavelength-shifted light 255. In particular embodiments, a luminescent detector 230 may be referred to as a luminescence-based detector, a photoluminescent detector, a photoluminescence-based detector, a fluorescent detector, or a fluorescence-based detector. In particular embodiments, luminescent detector 230 may include various optical, optoelectronic, or electronic components. In the example of FIG. 2, luminescent detector 230 includes a wavelength-shifting element 250, a concentrating element 260, and a detector 270. Although this disclosure describes and illustrates particular luminescent detectors that include particular components, this disclosure contemplates any suitable luminescent detectors that include any suitable components. In particular embodiments, a receiver 220 or a luminescent detector 230 may include a wavelength-shifting material that acts as a waveguide to guide an optical signal to a detector as disclosed in U.S. patent application Ser. No. 14/822,677, entitled "Multidirectional Communication System" and filed 10 Aug. 2015, which is incorporated herein by reference as an example and not by way of limitation.

As illustrated in FIG. 2, wavelength-shifting element 250 may be configured to receive input optical signal 240. In particular embodiments, wavelength-shifting element 250 may include a wavelength-shifting material configured to absorb at least a portion of the received optical signal 240 and produce wavelength-shifted light 255 from the absorbed portion of the optical signal 240. In particular embodiments, the wavelength-shifted light 255 may be referred to as emitted light, an emitted-light signal, radiated light, a radiated-light signal, or an emitted-optical signal. In particular embodiments, concentrating element 260 may be configured to receive at least a portion of the wavelength-shifted light 255 and concentrate the received portion of the wavelength-shifted light 255 to produce concentrated light 265 (which may be referred to as focused light). In particular embodiments, concentrating element 260 may include a refractive optical component (e.g., a lens, such as for example, a plano-convex lens or a Fresnel lens, or a refractive compound parabolic concentrator or other refractive parabolic condensing optics) or a reflective optical component (e.g., a concave mirror, an off-axis parabolic mirror, or a reflective compound parabolic concentrator or other reflective parabolic condensing optics). As an example and not by way of limitation, concentrating element 260 (which may be referred to as an optical-concentrating element or a focusing element) may include a lens that focuses the received wavelength-shifted light 255 onto detector 270. In particular embodiments, concentrating element 260 may include an imaging optical element (e.g., a lens) or a nonimaging optical element, such as for example, a plasmonic structure or a dielectric structure as described herein. In particular embodiments, luminescent detector 230 may include wavelength-shifting element 250 and detector 270, and luminescent detector 230 may not include a separate or discrete concentrating element 260. As an example and not by way of limitation, wavelength-shifting element 250 and concentrating element 260 may be integrated into a single element that produces light that is wavelength shifted and emitted in a concentrated or converging manner. The wavelength-shifting element 250 may include a plasmonic or dielectric structure configured to produce concentrated light 265 that is directed onto photodetector 270. In particular embodiments, detector 270 may be a photodetector that converts received light into an electrical current. As an example and not by way of limitation, photodetector 270 may be configured to receive concentrated light 265 from wavelength-shifting element 250 or concentrating element 260 and produce electrical current 275 corresponding to the received concentrated light 265. As illustrated in FIG. 2, the output electrical-current signal 275 from LD 230 may be supplied to a transimpedance amplifier 280.

Figure 3:
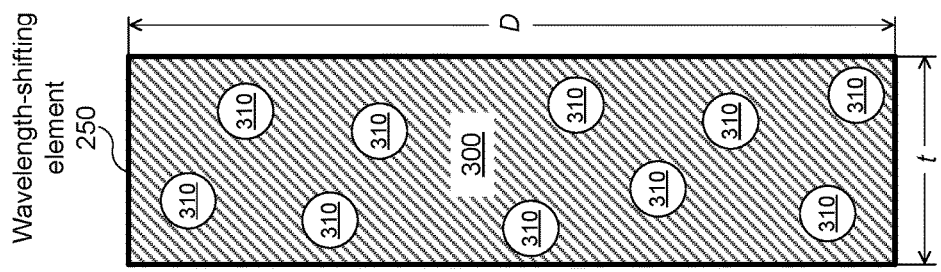
FIG. 3 illustrates an example wavelength-shifting element that includes a wavelength-shifting material.

FIG. 3 illustrates an example wavelength-shifting element 250 that includes a wavelength-shifting material 310. In particular embodiments, wavelength-shifting material 310 may include fluorescent dye, quantum dots, lattice defects, atomic or molecular materials (e.g., in gas, liquid, or solid phase), or fluorophores. In particular embodiments, wavelength-shifting material 310 may include a fluorescent dye that absorbs input light 240 over a particular range of wavelengths and produces wavelength-shifted light 255 from the absorbed light. The wavelength-shifted light may have a range of wavelengths that is longer than or shorter than the wavelength range of the absorbed light. As an example and not by way of limitation, the fluorescent dye may absorb input light 240 from approximately 375 nm to 425 nm and emit wavelength-shifted light 255 over a wavelength range of approximately 475 nm to 525 nm. As another example and not by way of limitation, wavelength-shifting material 310 may absorb input light 240 over a wavelength range that includes visible or near-infrared light, and the emitted wavelength-shifted light may have a wavelength range that is longer than or shorter than the wavelength range of the absorbed input light 240. In particular embodiments, wavelength-shifting material 310 may include quantum dots, which are nanoscale particles of semiconductor material having sizes of approximately 1 nm to 10 nm. As an example and not by way of limitation, wavelength-shifting material 310 may include cadmium selenide/cadmium sulfide (CdSe/CdS) quantum dots or lead selenide/lead sulfide (PbSe/PbS) quantum dots. Although this disclosure describes and illustrates particular wavelength-shifting materials that absorb and emit light at particular wavelengths, this disclosure contemplates any suitable wavelength-shifting materials that absorb and emit light at any suitable wavelengths.

In particular embodiments, wavelength-shifting element 250 may include an encapsulant material 300, and the wavelength-shifting material 310 may be contained within the encapsulant material 300. In particular embodiments, encapsulant material 300 may include a polymer or plastic material, such as for example, poly(methyl methacrylate) (which may be referred to as PMMA or acrylic), an acrylate-based polymer, polycarbonate, cyclic olefin copolymer (COC), or polyethersulfone (PES). As an example and not by way of limitation, wavelength-shifting material 310 may be contained within, distributed throughout, or incorporated into an encapsulant material 300. In particular embodiments, wavelength-shifting element 250 may be formed by combining a wavelength-shifting material 310 with an encapsulant material 300. As an example and not by way of limitation, a polymer material (e.g., PMMA) may be dissolved in an organic solvent (e.g., toluene, acetone, or methoxybenzene) to form a liquid, and a fluorescent dye may be mixed into the liquid. The polymer-solvent-dye mixture may then be spin-coated onto a substrate material (e.g., a transparent glass or plastic substrate), and after the solvent evaporates, a solid structure (e.g., wavelength-shifting element 250) may be formed where the fluorescent dye is encapsulated within the solid PMMA encapsulant 300. In particular embodiments, wavelength-shifting element 250 may be rigid (e.g., resistant to flexing by an applied force) or may be flexible. In particular embodiments, wavelength-shifting element 250 may be flat or may have a curved shape.

In particular embodiments, encapsulant material 300 may be substantially transparent. As an example and not by way of limitation, encapsulant material 300 alone (e.g., without wavelength-shifting material 310 present) may be substantially transparent to input optical light 240 or wavelength-shifted light 255. In particular embodiments, encapsulant material 300 (without wavelength-shifting material 310 present) being substantially transparent may refer to an encapsulant material 300 with thickness t having an optical transmission for optical signal 240 or wavelength-shifted light 255 of greater than or equal to 80%, 90%, or 95%. Although this disclosure describes and illustrates particular encapsulant materials having particular properties and being made from particular materials, this disclosure contemplates any suitable encapsulant materials having any suitable properties and being made from any suitable materials.

In particular embodiments, wavelength-shifting element 250 may have a thickness t of approximately 0.05 µm to approximately 1 mm. As an example and not by way of limitation, wavelength-shifting element 250 may have a thickness t of approximately 0.5 µm. In particular embodiments, wavelength-shifting element 250 may have a cross-sectional dimension D corresponding to a length, width, or diameter of a front or back surface of wavelength-shifting element 250. In the example of FIG. 3, wavelength-shifting element 250 is illustrated in a side view, and the front or back surface of wavelength-shifting element 250 may have a circular, elliptical, square, or rectangular shape with a particular length, width, or diameter. As an example and not by way of limitation, wavelength-shifting element 250 may have a substantially circular cross-sectional shape with a diameter D or a substantially square cross-sectional shape with dimensions D×D. In particular embodiments, dimension D of wavelength-shifting element 250 may be greater than or equal to 0.1 mm. As an example and not by way of limitation, dimension D may be approximately 0.1 mm to 20 cm. As another example and not by way of limitation, wavelength-shifting element 250 may have a substantially circular shape with a diameter D of approximately 5 cm and a thickness t of approximately 10 µm. In particular embodiments, dimension D may correspond to an input aperture of wavelength-shifting element 250. The input aperture of wavelength-shifting element 250 may represent an opening of wavelength-shifting element 250 or luminescent detector 230 through which input light 240 is received. As an example and not by way of limitation, dimension D may be 10 cm, and wavelength-shifting element 250 may be referred to as having a circular input aperture with a diameter of 10 cm. As another example and not by way of limitation, dimension D may be approximately 0.1 mm to 30 cm, and input aperture of wavelength-shifting element 250 may have a corresponding area of approximately 0.01 mm² to 1 m². Although this disclosure describes and illustrates particular wavelength-shifting elements having particular thicknesses and particular cross-sectional dimensions, this disclosure contemplates any suitable wavelength-shifting elements having any suitable thicknesses and any suitable cross-sectional dimensions.

Figure 4:
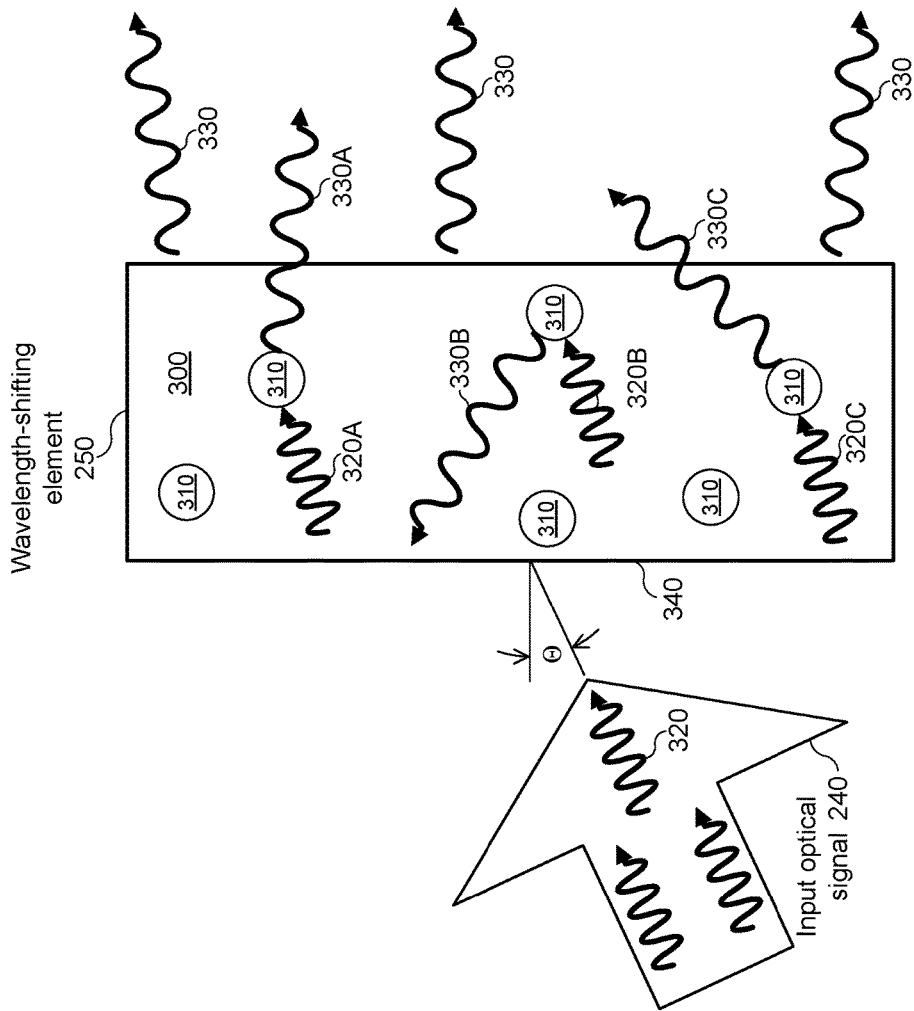
FIG. 4 illustrates an example wavelength-shifting element with an input optical signal.

FIG. 4 illustrates an example wavelength-shifting element 250 with an input optical signal 240. As discussed above, input optical signal 240 may be a free-space optical-communication signal (e.g., light from a modulated laser diode) sent from an optical transmitter 210. As illustrated in FIG. 4, input optical signal 240 may be made up of a collection of input photons 320. Similarly, the wavelength-shifted light 255 may be made up of photons 330 that are emitted by wavelength-shifting material 310. In particular embodiments, an input photon 320 may be absorbed by a particle of wavelength-shifting material 310, and the wavelength-shifting material 310 may then emit a photon 330. In particular embodiments, a process of absorbing an input photon 320 that results in the emission of another photon 330 as illustrated in the example of FIG. 4 may be referred to as luminescence, photoluminescence, or fluorescence. In FIG. 4, input photons 320A, 320B, and 320C are each absorbed by a particle of wavelength-shifting material 310, which then results in the emission of photons 330A, 330B, and 330C, respectively. As an example and not by way of limitation, wavelength-shifting material 310 may be a fluorescent dye. A molecule of fluorescent dye may absorb an input photon 320 and transition from a ground state into an excited energy state. The dye molecule may relax through one or more non-radiative transitions into a lower energy state, and then the dye molecule may emit a photon 330 and relax back into its ground state.

In particular embodiments, the average time that a particle of wavelength-shifting material 310 remains in an excited state before emitting photon 330 may be referred to as an upper-state lifetime, excited-state lifetime, radiative lifetime, fluorescence lifetime, or decay time. In particular embodiments, the wavelength-shifted light 255 emitted by wavelength-shifting element 250 may exhibit a power or intensity that decays exponentially with time based on the upper-state lifetime τ. As an example and not by way of limitation, if the wavelength-shifting element 250 is illuminated by a short pulse of light, the resulting wavelength-shifted light 255 may be emitted with an optical intensity I that varies with time as $I(t)=I_0 e^{-t/\tau}$, where $I_0$ represents an initial, peak intensity value at t=0. In particular embodiments, wavelength-shifting material 310 may have an upper-state lifetime (τ) of less than or equal to 10 nanoseconds. As an example and not by way of limitation, the wavelength-shifting material 310 may be a fluorescent dye with an upper-state lifetime of approximately 1.5 nanoseconds. As another example and not by way of limitation, the wavelength-shifting material 310 may have an upper-state lifetime of approximately 10-100 picoseconds. In particular embodiments, the upper-state lifetime of wavelength-shifting material 310 may be reduced by application of the Purcell effect, which relates to changing the upper-state lifetime of a fluorescent material by a modifying the material's environment. As an example and not by way of limitation, wavelength-shifting material 310 may be combined with another material (e.g., encapsulant material 300) or with a structure (e.g., a resonant optical cavity or a plasmonic material) to result in a reduced upper-state lifetime. As another example and not by way of limitation, a wavelength-shifting material 310 with a 1-2 nanosecond upper-state lifetime may have its upper-state lifetime reduced to 10-100 picoseconds by including a material or structure in the wavelength-shifting element 250 that reduces the upper-state lifetime through the Purcell effect. In particular embodiments, the upper-state lifetime of wavelength-shifting material 310 may be reduced by incorporating the wavelength-shifting material 310 into encapsulant 300. As an example and not by way of limitation, the upper-state lifetime of the wavelength-shifting material 310 may be reduced due to an interaction with or due to properties of the surrounding encapsulant material 300. In particular embodiments, the quantum efficiency of wavelength-shifting material 310 may be increased due to an interaction with or due to properties of the surrounding encapsulant material 300. As an example and not by way of limitation, the optical absorption of the wavelength-shifting material 310 may be increased due to an interaction with or due to properties of the surrounding encapsulant material 300. Although this disclosure describes and illustrates particular wavelength-shifting materials having particular upper-state lifetimes, this disclosure contemplates any suitable wavelength-shifting materials having any suitable upper-state lifetimes.

In particular embodiments, an emitted photon 330 may have less energy or a longer wavelength than an input photon 320. As an example and not by way of limitation, the absorbed photons 320 may have a wavelength range that includes visible or near-infrared light, and the emitted photons 330 may have a wavelength range that is longer than the wavelength range of the absorbed photons 320. As another example and not by way of limitation, the absorbed photons 320 may have wavelengths of approximately 390-420 nm, and the emitted photons 330 may have wavelengths of approximately 470-530 nm. As another example and not by way of limitation, the absorbed photons 320 may have a peak absorption wavelength around 405 nm, and the emitted photons 330 may have a peak emission wavelength around 490 nm. As another example and not by way of limitation, the absorbed photons 320 may have wavelengths of approximately 700-750 nm, and the emitted photons 330 may have wavelengths of approximately 760-800 nm. As another example and not by way of limitation, the absorbed photons 320 may have wavelengths of approximately 1.4-1.5 µm, and the emitted photons 330 may have wavelengths of approximately 1.5-1.6 µm. In particular embodiments, an emitted photon 330 may have more energy or a shorter wavelength than an input photon 320. As an example and not by way of limitation, the absorbed photons 320 may have a wavelength range that includes visible or near-infrared light, and the emitted photons 330 may have a wavelength range that is shorter than the wavelength range of the absorbed photons 320. Although this disclosure describes and illustrates particular absorbed and emitted photons having particular wavelengths, this disclosure contemplates any suitable absorbed and emitted photons having any suitable wavelengths.

In particular embodiments, the wavelength-shifting material 310 of wavelength-shifting element 250 may absorb greater than or equal to 70% of input optical signal 240. As an example and not by way of limitation, wavelength-shifting element 250 may absorb greater than 80%, 90%, or 98% of input optical signal 240. As another example and not by way of limitation, for every 100 input photons 320 of input optical signal 240, greater than or equal to 70 of the input photons 320 may be absorbed by wavelength-shifting material 310 of wavelength-shifting element 250. As another example and not by way of limitation, wavelength-shifting element 250 may have an optical transmission of less than 2%, 10%, or 20% for light of input optical signal 240. In particular embodiments, the optical absorption of wavelength-shifting element 250 for emitted photons 330 may be less than or equal to 20%. As an example and not by way of limitation, the absorption of wavelength-shifting element 250 for emitted photons 330 may be less than 10%, 5%, or 2%. In particular embodiments, wavelength-shifting element 250 may be substantially absorptive to photons 320 of input optical signal 240 and may be substantially transmissive to emitted photons 330. As an example and not by way of limitation, wavelength-shifting element 250 may absorb greater than 80% of input optical signal 240 and may absorb less than 20% of emitted photons 330. As another example and not by way of limitation, wavelength-shifting element 250 may have an optical absorption of ≥95% for 375-425 nm light and an optical absorption of ≤10% for 475-525 nm light. Although this disclosure describes and illustrates particular wavelength-shifting elements having particular absorptions at particular wavelengths, this disclosure contemplates any suitable wavelength-shifting elements having any suitable absorptions at any suitable wavelengths.

In the example of FIG. 4, input optical beam 240 has an angle of incidence $\Theta$ of approximately 25° with respect to the front surface 340 of wavelength-shifting element 250. In particular embodiments, the angle of incidence $\Theta$ of input optical beam 240 may be any suitable angle. As an example and not by way of limitation, the input optical beam 240 may be incident on the wavelength-shifting element 250 at an angle $\Theta$ of 0° to approximately ±45°, where a zero-degree incidence angle represents normal incidence with respect to the front surface 340 of wavelength-shifting element 250. As another example and not by way of limitation, optical beam 240 may have an angle of incidence $\Theta$ with respect to the front surface 340 of wavelength-shifting element 250 within the range of ±25°, ±15°, ±5°, or within any suitable angular range. In particular embodiments, the absorption of input optical signal 240 by wavelength-shifting element 250 may be substantially uniform regardless of the angle of incidence $\Theta$. As an example and not by way of limitation, the absorption of wavelength-shifting element 250 may be approximately equal to 95% for input optical signal 240 having any angle of incidence $\Theta$ within a range of ±25°. As another example and not by way of limitation, the absorption of input optical signal 240 by wavelength-shifting element 250 may vary by less than any suitable amount (e.g., less than 10%, 5%, 2%, or 1%) as the angle of incidence $\Theta$ is varied over a particular range (e.g., over ±25°, ±15°, or)±5°. In particular embodiments, an angular range over which wavelength-shifting element 250 may receive and absorb light of input optical signal 240 may be referred to as a field of view (FOV). As an example and not by way of limitation, if the absorption of input optical signal 240 is substantially constant for angles of incidence $\Theta$ within a ±25° range, then wavelength-shifting element 250 or luminescent detector 230 may be referred to as having a ±25-degree FOV or a 50-degree FOV. Although this disclosure describes and illustrates particular optical beams having particular angles of incidence, this disclosure contemplates any suitable optical beams having any suitable angles of incidence.

Figure 5:
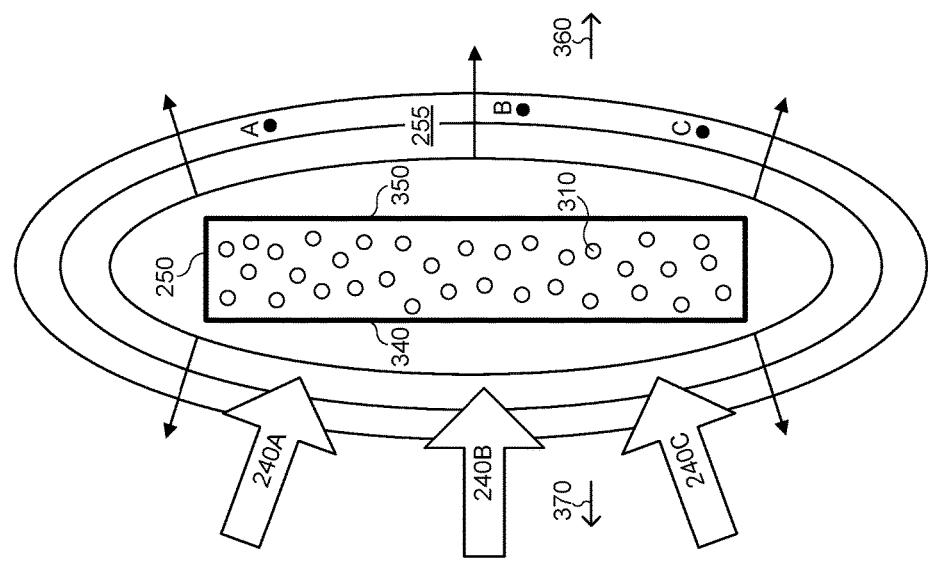
FIG. 5 illustrates an example wavelength-shifting element with input optical signals and an emitted optical signal.

FIG. 5 illustrates an example wavelength-shifting element 250 with input optical signals 240A, 240B, and 240C and an emitted-optical signal 255. Each input optical signal 240A-240C may represent a different optical signal 240 with a particular angle of incidence $\Theta$ with respect to front surface 340. In the example of FIG. 5, input beams 240A, 240B, and 240C have angles of incidence $\Theta$ of approximately −20°, 0°, and +20°, respectively. In particular embodiments, emitted-optical signal 255 may include photons 330 emitted by wavelength-shifting material 310. In particular embodiments, each particle of wavelength-shifting material 310 may be an isotropic emitter that emits photons 330 in any direction with equal probability. As an example and not by way of limitation, photons 330 may be emitted substantially evenly in all directions by wavelength-shifting material 310 resulting in a substantially isotropic or uniform emitted-optical signal 255. As another example and not by way of limitation, for a given input optical signal 240A, 240B, or 240C, the intensity of emitted-optical signal 255 along the front surface 340 or the back surface 350 of wavelength-shifting element 250 may vary by less than 10%. In particular embodiments, the emitted-optical signal 255 may be substantially insensitive to the angle of incidence Θ of input optical signal 240. As an example and not by way of limitation, for each input beam 240A, 240B, or 240C, the emitted-optical signal 255 may have substantially the same wavelength range and the same optical intensity. As another example and not by way of limitation, the intensity of emitted-optical signal 255 at each of points A, B, and C may vary by less than 10% as the angle of incidence Θ is varied from −20° to +20°.

In particular embodiments, wavelength-shifting material 310 may be a non-isotropic emitter that preferentially radiates emitted-light signal 255 in a forward direction 360 or a backward direction 370. In FIG. 5, arrows 360 and 370 represent forward and backward directions, respectively. Forward direction 360 points away from wavelength-shifting element 250 and along the same direction as input beam 240B, and backward direction 370 points away from wavelength-shifting element 250 and opposite to input beam 240B. In particular embodiments, light emitted in the forward direction 360 may refer to light emitted within a particular angle of forward direction 360. As an example and not by way of limitation, light emitted in the forward direction 360 may include light emitted within ±1°, ±5°, ±10°, ±20°, or within any suitable angular range of forward direction 360. Similarly, light emitted in the backward direction 370 may include light emitted within ±1°, ±5°, ±10°, ±20°, or within any suitable angular range of backward direction 370.

In particular embodiments, a non-isotropically-emitting wavelength-shifting element 250 may produce emitted light 255 that is substantially directed along the forward direction 360 or the backward direction 370. As an example and not by way of limitation, wavelength-shifting material 310 may be configured to act as a directional emitter that emits light signal 255 mostly in the forward and backward directions 360 and 370. As another example and not by way of limitation, greater than or equal to 80% of emitted light 255 may be directed along the forward 360 or backward 370 direction, and less 20% of emitted light 255 may be directed off to the sides of wavelength-shifting element 250. As another example and not by way of limitation, greater than or equal to 40% of emitted light 255 may be directed within ±10° of forward direction 360, and greater than or equal to 40% of emitted light 255 may be directed within ±10° of backward direction 370. The remaining less-than 20% portion of emitted light may be directed off to the sides of wavelength-shifting element 250 (e.g., directed at angles greater than 10° with respect to forward direction 360 or backward direction 370). In particular embodiments, wavelength-shifting element 250 may produce emitted light 255 substantially along forward direction 360 or backward direction 370 regardless of the angle of incidence Θ of input optical signal 240. As an example and not by way of limitation, emitted light 255 may be directed substantially along forward 360 or backward 370 direction as the angle of incidence Θ is varied from −20° to +20°. Although this disclosure describes and illustrates particular wavelength-shifting elements that produce particular isotropic or particular non-isotropic emitted-light signals, this disclosure contemplates any suitable wavelength-shifting elements that produce any suitable isotropic or any suitable non-isotropic emitted-light signals.

In particular embodiments, front surface 340 or back surface 350 of wavelength-shifting element 250 may include a dielectric coating. In particular embodiments, a dielectric coating may refer to one or more thin-film layers of one or more dielectric materials (e.g., magnesium fluoride, silicon dioxide, tantalum pentoxide, zinc sulfide, or titanium dioxide) deposited on front surface 340 or back surface 350 by vacuum deposition (e.g., evaporation or sputtering). In particular embodiments, a dielectric coating may act as an anti-reflection (AR) coating that reduces the optical reflectivity or loss of a surface due to specular reflection. As an example and not by way of limitation, an AR-coating applied to front surface 340 may reduce the reflectivity of front surface 340 to input light 240A-240C from approximately 5% to less than 1%, 0.5%, or any suitable reflectivity. Similarly, an AR-coating applied to back surface 350 may reduce the reflectivity of back surface 350 to emitted light 255 from approximately 4% to less than 0.5%. A front-surface AR-coating may increase the amount of input light 240 that reaches wavelength-shifting material 310 by reducing the reflectivity of front surface 340. A back-surface AR-coating may increase the amount of emitted photons 330 that exit from wavelength-shifting element 250 by reducing the reflectivity of back surface 350. In particular embodiments, a dielectric coating may act as a high-reflection (HR) coating that increases the optical reflectivity of a surface. As an example and not by way of limitation, an HR-coating applied to front surface 340 may provide a reflectivity of ≥80% to emitted light 255. A front-surface HR-coating may reflect some of the emitted photons 330 so that they are redirected along the forward direction 360. In particular embodiments, a dielectric coating may act as an AR-coating for one range of wavelengths and an HR-coating for another range of wavelengths. As an example and not by way of limitation, a dielectric coating applied to front surface 340 may act as an AR-coating for input light 240 and an HR-coating for emitted light 255. As another example and not by way of limitation, a dielectric coating applied to front surface 340 may have a reflectivity of ≤1% from approximately 375 nm to 425 nm and a reflectivity of ≥90% from approximately 475 nm to 525 nm. Although this disclosure describes and illustrates particular dielectric coatings having particular reflectivity at particular wavelengths, this disclosure contemplates any suitable dielectric coatings having any suitable reflectivity at any suitable wavelengths.

Figure 6:
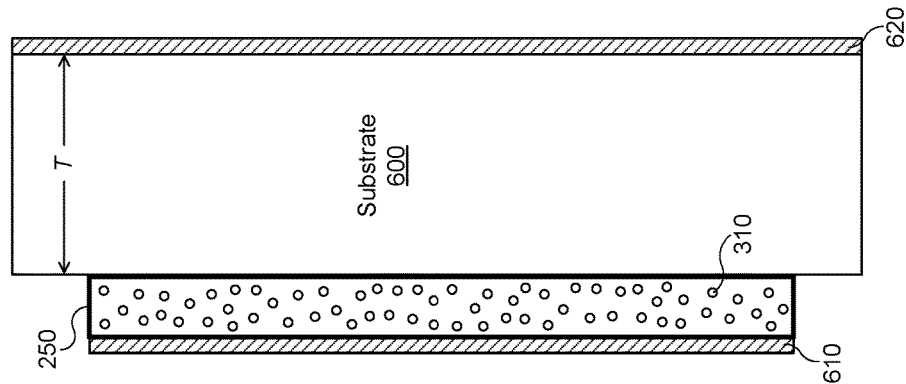
FIG. 6 illustrates an example wavelength-shifting element affixed to an example substrate.

FIG. 6 illustrates an example wavelength-shifting element 250 affixed to an example substrate 600. In particular embodiments, substrate 600 may be a substantially transparent material, such as for example glass (e.g., fused silica), plastic, or polymer (e.g., PMMA). As an example and not by way of limitation, substrate 600 may have an optical transmission for optical signal 240 or emitted light 255 of greater than or equal to 80%, 90%, or 95%. In particular embodiments, substrate 600 may have a thickness T of approximately 0.5 mm to 10 mm. As an example and not by way of limitation, substrate 600 may have a thickness T of approximately 1 mm. In particular embodiments, wavelength-shifting element 250 may be affixed to substrate 600 by spin-coating or by use of an adhesive or epoxy. As an example and not by way of limitation, a polymer-solvent-dye mixture may be spin-coated directly onto substrate 600 resulting in a wavelength-shifting element 250 which is attached to substrate 600. Although this disclosure describes and illustrates particular substrates made from particular materials and having particular dimensions, this disclosure contemplates any suitable substrates made from any suitable materials and having any suitable dimensions.

In particular embodiments, an input light signal 240 may be incident on wavelength-shifting element 250 in FIG. 6 from the right or left. In particular embodiments, wavelength-shifting element 250 may include dielectric coating 610 that acts as an AR-coating, an HR-coating, or a combined AR/HR-coating. As an example and not by way of limitation, input light 240 may be incident on wavelength-shifting element 250 from the left, and dielectric coating 610 may act as an AR-coating for input light 240. As another example and not by way of limitation, dielectric coating 610 may be a combined AR/HR-coating that acts as an AR-coating for input light 240 and an HR-coating for emitted light 255. As another example and not by way of limitation, input light 240 may be incident on wavelength-shifting element 250 from the right (e.g., input light 240 may pass through substrate 600 first before encountering wavelength-shifting element 250), and dielectric coating 610 may be an AR-coating for emitted light 255. In particular embodiments, substrate 600 may include dielectric coating 620 that acts as an AR-coating, an HR-coating, or a combined AR/HR-coating. As an example and not by way of limitation, input light 240 may be incident on wavelength-shifting element 250 from the left, and dielectric coating 620 may act as an AR-coating for emitted light 255. As another example and not by way of limitation, input light 240 may be incident on wavelength-shifting element 250 from the right, and dielectric coating 620 may be an AR-coating for input light 240. As another example and not by way of limitation, dielectric coating 620 may be a combined AR/HR-coating that acts as an AR-coating for input light 240 and an HR-coating for emitted light 255. Although this disclosure describes and illustrates particular dielectric coatings applied to particular surfaces, this disclosure contemplates any suitable dielectric coatings applied to any suitable surfaces.

Figure 7:
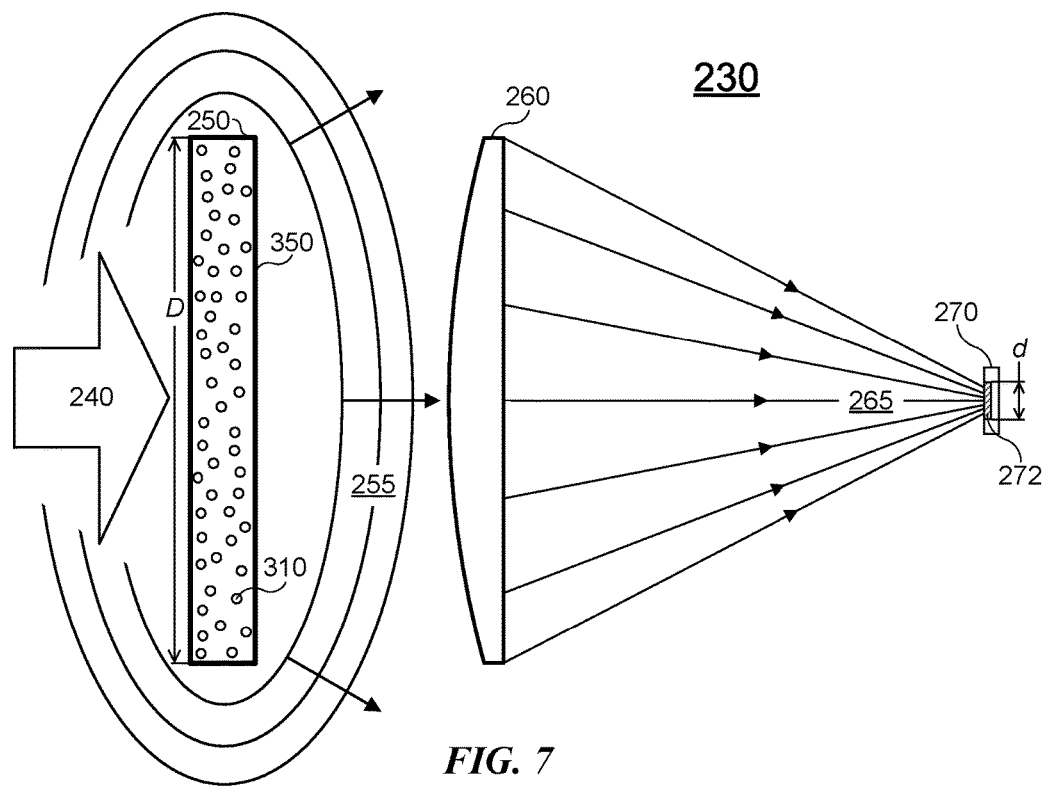
FIG. 7 illustrates an example luminescent detector.

FIG. 7 illustrates an example luminescent detector 230. In particular embodiments, luminescent detector 230 may include wavelength-shifting element 250, concentrating element 260, and photodetector 270. As illustrated in FIG. 7, wavelength-shifting element 250 may be configured to receive input optical signal 240 and, through a fluorescence process, produce emitted-light signal 255. A portion of emitted-light signal 255 may be received by concentrating element 260, which produces concentrated light 265, and the concentrated light 265 is directed or concentrated onto active region 272 of photodetector 270.

In particular embodiments, concentrating element 260 may be a lens or a nonimaging optical element positioned between wavelength-shifting element 250 and photodetector 270. As an example and not by way of limitation, lens 260 may be a plano-convex lens (as illustrated in FIG. 7), a Fresnel lens (e.g., a Fresnel lens may be incorporated into or attached to the back surface of wavelength-shifting element 250), or any other suitable lens. In particular embodiments, lens 260 may include a dielectric coating on one or more of its surfaces. As an example and not by way of limitation, lens 260 may include AR-coatings on its input and output surfaces to provide reduced reflectivity for emitted light 255. In particular embodiments, lens 260 may be positioned behind wavelength-shifting element 250 (e.g., opposite the side upon which input beam 240 is incident) and may be configured to capture at least a portion of the emitted light 255 that passes through back surface 350 of wavelength-shifting element 250. In particular embodiments, lens 260 may be located any suitable distance from wavelength-shifting element. As an example and not by way of limitation, lens 260 may be in contact with or attached to back surface 350 of wavelength-shifting element 250 (e.g., lens 260 may be affixed with an optically clear adhesive to back surface 350, or lens 260 may be a Fresnel lens integrated into back surface 350). As another example and not by way of limitation, lens 260 may be located 0 mm to approximately 200 mm from back surface 350 of wavelength-shifting element 250. In particular embodiments, concentrating element 260 may be combined with or integrated into wavelength-shifting element 250. As an example and not by way of limitation, luminescent detector 230 may not include a separate or discrete concentrating element 260. As another example and not by way of limitation, the concentrating element 260 may be incorporated into wavelength-shifting element 250, and the concentrating of emitted light 255 may be performed by wavelength-shifting element 250 (e.g., by a plasmonic or dielectric structure contained within wavelength-shifting element 250).

In particular embodiments, lens 260 may have any suitable diameter and any suitable focal length. As an example and not by way of limitation, lens 260 may have a diameter that is approximately the same size as dimension D of wavelength-shifting element 250. As another example and not by way of limitation, lens 260 may have a focal length of approximately 25 mm to 250 mm. As another example and not by way of limitation, wavelength-shifting element 250 may have a dimension D of approximately 50 mm, and lens 260 may have a 50-mm diameter and a 50-mm focal length. In particular embodiments, photodetector 270 and lens 260 may be separated by a distance that is approximately equal to the focal length of lens 260. As an example and not by way of limitation, lens 260 may have a 100-mm focal length, and the distance between lens 260 and photodetector 270 may be approximately 100 mm. Although this disclosure describes and illustrates particular types of lenses having particular positions, diameters, or focal lengths, this disclosure contemplates any suitable types of lenses having any suitable positions, diameters, or focal lengths.

In particular embodiments, photodetector 270 may receive concentrated light 265 from concentrating element 260 and produce an electrical current 275 corresponding to the received concentrated light 265. As an example and not by way of limitation, if the concentrated light 265 received by photodetector 270 has a peak power of 1 mW, then the corresponding current 275 produced by photodetector 270 may have a peak amplitude of 0.8 mA (which corresponds to photodetector 270 having an optical responsivity of 0.8 A/W). In particular embodiments, photodetector 270 may be a photodiode, such as for example, a semiconductor diode structure that converts received light 265 into an electrical current 275. As an example and not by way of limitation, photodetector 270 may be a silicon photodiode, germanium photodiode, indium-gallium-arsenide photodiode, or mercury-cadmium-telluride photodiode. As another example and not by way of limitation, photodetector 270 may be a photodiode with an optical responsivity of 0.1 to 1 amperes per watt (A/W) of incident optical power. As another example and not by way of limitation, photodetector 270 may be a photodiode with an active region 272 having a width d or a diameter d of less than or equal to 1 mm (e.g., active region 272 may have a diameter d of 100 µm). The active region 272 may refer to an area of photodetector 270 that is sensitive to light (e.g., the active region 272 converts input light into electrical current). As another example and not by way of limitation, photodetector 270 may be a photodiode with an active region 272 having an area of less than or equal to 1 mm² (e.g., active region 272 may have an area of 0.1 mm²). As another example and not by way of limitation, photodetector 270 may be an avalanche photodiode (APD) that produces electrons from received light and then provides gain through avalanche multiplication. Although this disclosure describes and illustrates particular photodetectors having particular active regions with particular dimensions, this disclosure contemplates any suitable photodetectors having any suitable active regions with any suitable dimensions.

In particular embodiments, photodetector 270 may be a photodiode with a response time (e.g., a rise time or a fall time) that is approximately equal to or faster than the upper-state lifetime τ of wavelength-shifting material 310. As an example and not by way of limitation, photodetector 270 may have a rise time of less than or equal to 2 nanoseconds. As another example and not by way of limitation, photodetector 270 may have a rise time of less than or equal to 100 picoseconds. In particular embodiments, luminescent detector 230 may have an input aperture with an area $A_{LD}$, (e.g., $A_{LD}$ may correspond to the input aperture of wavelength-shifting element 250), and photodetector 270 may have an active region 272 with an area $A_{PD}$. As an example and not by way of limitation, $A_{LD}$ may be approximately 1 cm² to 400 cm², and $A_{PD}$ may be approximately 0.0001 mm² to 1 mm². As another example and not by way of limitation, input aperture may have a diameter D greater than or equal to 1 cm, and photodetector active region 272 may have a diameter d less than or equal to 1 mm. As another example and not by way of limitation, input aperture may have a diameter D greater than or equal to 1 mm, and photodetector active region 272 may have a diameter d less than or equal to 20 µm. In particular embodiments, the ratio $A_{LD}/A_{PD}$ may be referred to as an active-region gain and may represent an effective increase in the area of the active region of photodetector 270 provided by the structure of luminescent detector 230. As an example and not by way of limitation, for a luminescent detector 230 having an input aperture with diameter D=50 mm and a photodetector active region 272 with a diameter d=1 mm, the active-region gain is $D^2/d^2$=2500. This provides a luminescent detector 230 having an effective area that is 2500 times larger than the area of active region 272 without significantly sacrificing the speed of the photodetector 270. In particular embodiments, the optical power loss (e.g., due to atmospheric effects, such as for example, atmospheric absorption and turbulence) between a transmitter 210 and a receiver 220 may be approximately 30-60 dB. As an example and not by way of limitation, for a transmitter 210 that produces an average optical output power of 100 mW, a 50-dB optical loss between the transmitter 210 and receiver 220 may result in approximately 1 µW of received optical power at receiver 220 (e.g., the received power is reduced by 50 dB, or a factor of $10^{-5}$). In particular embodiments, by boosting the amount of light captured by receiver 220, a receiver 220 with an active-region gain of $A_{LD}/A_{PD}$ may result in an effective $A_{LD}/A_{PD}$ reduction in the transmitter-to-receiver optical loss. As an example and not by way of limitation, for a 50-dB optical loss between transmitter 210 and receiver 220, an active-region gain of 1000× may reduce the optical loss by 30 dB, resulting in an effective optical loss between transmitter 210 and receiver 220 of 20 dB. In particular embodiments, a luminescent detector 230 may behave as a detector having an active region with an effective area $A_{LD}$ and a speed (e.g., a rise time or fall time) based on the speed of photodetector 270. Luminescent detector 230 may perform as a detector having a relatively large effective area $A_{LD}$ while still maintaining the relatively fast response time provided by the relatively small photodetector 270. Additionally, luminescent detector 230 may exhibit a fairly large field of view (e.g., FOV≥50°), while a conventional detector with a comparable lens and photodetector (and with no wavelength-shifting element) may exhibit a fairly limited field of view (e.g., FOV≤2°).

In particular embodiments, concentrating element 260 may capture a portion of emitted-light signal 255 produced by the wavelength-shifting material 310 of wavelength-shifting element 250. In particular embodiments, concentrating element 260 may receive greater than or equal to 25% of the total emitted-light signal 255. As an example and not by way of limitation, wavelength-shifting material 310 may be an isotropic emitter that emits photons 330 in all directions with equal probability, and concentrating element 260 may be configured to capture at least 25% of the emitted-light signal 255. As another example and not by way of limitation, wavelength-shifting material 310 may be a non-isotropic emitter configured to radiate most of the emitted-light signal 255 in the forward direction (e.g., toward concentrating element 260) or in the backward direction. In this case, concentrating element 260 may receive greater than or equal to 40% of the total emitted-light signal 255.

In particular embodiments, input optical beam 240 may exhibit a distorted, nonuniform, or time-varying distribution of incidence angles (which may be referred to as having a distorted, nonuniform, or time-varying wavefront or phase front). In particular embodiments, input optical beam 240 may exhibit significant wavefront distortion resulting from atmospheric turbulence as optical beam 240 propagates from transmitter 210 to receiver 220. Additionally, the wavefront distortion of input optical beam 240 may be time varying since atmospheric turbulence may be associated with irregular air motions that exhibit time-varying changes in speed and direction.

In particular embodiments, wavelength-shifting element 250 may reduce or eliminate problems associated with input light signal 240 having a distorted wavefront. As an example and not by way of limitation, the wavelength-shifting element 250 may absorb input photons 320 from the input light signal 240 regardless of the wavefront shape of input light signal 240 and with an optical efficiency that depends primarily on the material and structure of wavelength-shifting element 250 and on whether it includes a plasmonic or dielectric structure. The emitted photons 330 of emitted light 255 may have no fixed or definite phase relationship with input photons 320. The emitted light 255 may have no time coherence over the area of the wavelength-shifting element 250 but may be highly directional depending on the plasmonic or dielectric material included with the wavelength-shifting element 250. Regardless of whether the input optical signal 240 has a distorted, nonuniform, or time-varying distribution of incidence angles, the emitted light 255 from the wavelength-shifting element 250 may have a substantially directional character. As an example and not by way of limitation, the wavelength-shifted light 255 may be emitted primarily in the forward or backward directions or may be emitted as concentrated light that converges on detector 270.

In particular embodiments, a luminescent detector 230 as described herein may offer a relatively large effective detector area, a relatively fast response time, a relatively large FOV, and relative insensitivity to wavefront distortion or phase fluctuations of input optical signal 240. As an example and not by way of limitation, luminescent detector 230 may have an input aperture with an area of greater than 25 cm$^2$, a response time of less than 1 nanosecond, and a FOV of greater than 25 degrees. Additionally, luminescent detector 230 may have the ability to receive and detect input light 240 in a manner that is substantially insensitive to the wavefront distortion, phase variation, or mode quality of the input light 240.

Previous approaches to detecting a free-space optical communication signal may employ a receiver with a lens that focuses received light onto a photodetector. However, such conventional approaches may have difficulty effectively focusing received light onto a relatively small photodetector since the received light can exhibit significant wavefront distortion caused by atmospheric turbulence as the optical signal propagates from the transmitter to the receiver. A beam with significant wavefront distortion may be focused to a distorted or relatively large spot (e.g., the focused beam spot may be larger than the active region of the photodetector). Moreover, a conventional receiver may have a relatively narrow FOV, and since the wavefront distortion can vary with time, the coupling of the light onto the detector can similarly vary with time (e.g., time-varying distribution of incidence angles can cause the focused beam spot to move laterally with respect to the photodetector), resulting in undesirable amplitude fluctuations in the output electronic signal produced by a conventional receiver.

In particular embodiments, a luminescent detector 230 that includes a wavelength-shifting element 250 as described herein may mitigate the shortcomings of conventional receivers. Since emitted light 255 may exhibit highly directional output depending on the structure of wavelength-shifting element 250 and not on the wavefront of input light 240, the emitted light 255 can be effectively concentrated to a small spot (e.g., by parabolic condensing optics 260). Additionally, even though the distribution of incidence angles of the input light 240 may vary in time due to atmospheric turbulence, the concentrated light 265 may remain concentrated onto the active region 272 (without exhibiting significant lateral motion), resulting in significantly reduced amplitude fluctuations in electrical current 275. Moreover, the large effective area, the large FOV, and the relative insensitivity to incidence angle provided by luminescent detector 230 may reduce the requirements for beam pointing accuracy and tracking for transmitter 210. An active tracking system on the transmitter side may not be required or the performance requirements for a tracking system may be relaxed since luminescent detector 230 may tolerate some amount of movement or angular variation of optical beam 240.

Figure 8:
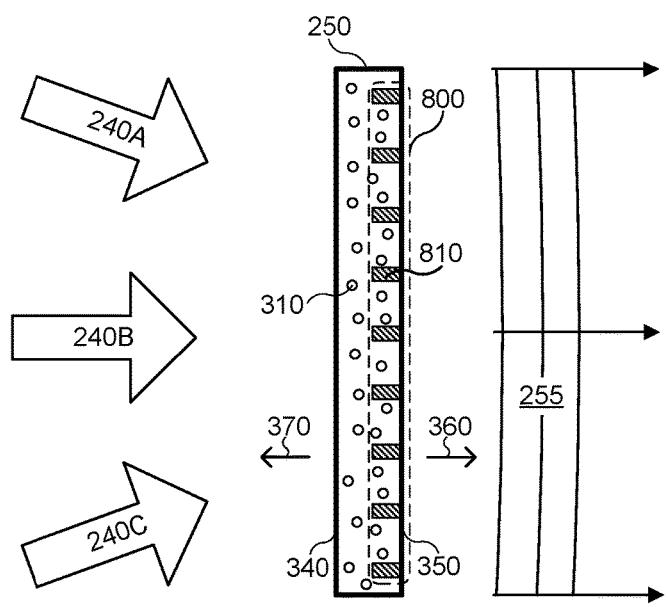
FIG. 8 illustrates an example wavelength-shifting element that includes an example plasmonic or dielectric structure.

FIG. 8 illustrates an example wavelength-shifting element 250 that includes an example plasmonic or dielectric structure 800. In particular embodiments, wavelength-shifting element 250 may include wavelength-shifting material 310 and a plasmonic structure 800 or a dielectric structure 800. A plasmonic structure 800 may refer to a metallic microstructure in which plasma oscillations (or, plasmons) may be induced by electromagnetic radiation (e.g., by emitted light 255). The emitted light 255 from wavelength-shifting material 310 may be coupled to plasmonic structure 800 resulting in the generation of plasmons in or on the surface of plasmonic structure 800. In the example of FIG. 8, plasmonic structure 800 is represented schematically by an arrangement of plasmonic-structure elements 810 surrounded by a dashed line. In particular embodiments, plasmonic structure 800 (which may be referred to as a plasmonic grating 800) may be a metallic microstructure that includes a periodic or non-periodic arrangement of any suitable number (e.g., $10^2$ to $10^{12}$) of plasmonic-structure elements 810, and each element 810 may have a dimension on the order of 10 nanometers to 1 μm. As an example and not by way of limitation, plasmonic structure 800 may include plasmonic-structure elements 810 with a 0.1-μm length or diameter, and the elements 810 may be located approximately 1 μm apart. In particular embodiments, plasmonic-structure elements 810 may have any suitable shape (e.g., substantially spherical, elliptical, or rectangular), and the elements 810 may be made from any suitable electrically conductive material (e.g., aluminum, copper, silver, or gold). In particular embodiments, wavelength-shifting element 250 may include wavelength-shifting material 310 and a dielectric structure 800. As an example and not by way of limitation, wavelength-shifting element 250 may include a structure made up of dielectric material embedded or contained within wavelength-shifting element 250. As another example and not by way of limitation, wavelength-shifting element 250 may include a dielectric grating 800 doped with wavelength-shifting material 310.

In particular embodiments, plasmonic or dielectric structure 800 may be located within wavelength-shifting element 250 or may be located on the front surface 340 or back surface 350 of wavelength-shifting element 250. In particular embodiments, plasmonic or dielectric structure 800 may be located within wavelength-shifting element 250 and between front surface 340 and back surface 350. As illustrated in FIG. 8, plasmonic or dielectric structure 800 may be located within wavelength-shifting element 250 and adjacent to back surface 350. In particular embodiments, each particle of wavelength-shifting material 310 may be located within approximately 1 μm of one or more plasmonic-structure elements 810 of plasmonic structure 800, which may allow the emitted light 255 to interact with or couple to the plasmonic structure 800. In particular embodiments, plasmonic or dielectric structure 800 may be deposited or stamped onto a surface of a substrate 600, and then the wavelength-shifting element 250 may be fabricated on the same surface of substrate 600 (e.g., by spin-coating, as described above). Although this disclosure describes and illustrates particular wavelength-shifting elements having particular plasmonic or dielectric structures with particular dimensions, this disclosure contemplates any suitable wavelength-shifting elements having any suitable plasmonic or dielectric structures with any suitable dimensions.

In particular embodiments, wavelength-shifting element 250 may include a plasmonic or dielectric structure 800 that causes the emitted light 255 to be radiated from the wavelength-shifting element 250 in a directional manner. As an example and not by way of limitation, the plasmonic-structure elements 810 of plasmonic structure 800 may act as tiny antennas that cause the emitted light 255 to be radiated primarily in the forward direction 360 or backward direction 370. The emitted light 255 radiated in the forward direction 360 and backward direction 370 may include greater than 80% of the total emitted-light signal 255. As another example and not by way of limitation, a wavelength-shifting element 250 that includes wavelength-shifting material 310 and a plasmonic or dielectric structure 800 may radiate greater than or equal to 40% of the total emitted-light signal 255 in the forward direction 360. In particular embodiments, wavelength-shifting element 250 may include a plasmonic or dielectric structure 800 that receives a portion of the emitted light 255 and causes the received portion of emitted light 255 to be concentrated as a converging beam (e.g., concentrated light 265) directed onto active region 272 of photodetector 270. As an example and not by way of limitation, a plasmonic or dielectric structure 800 may be configured so that emitted light 255 is emitted in a concentrated or converging manner. The emitted light 255 may be concentrated directly onto active region 272 of photodetector 270 without the need for a separate, discrete focusing element located outside of the wavelength-shifting element 250. In particular embodiments, a wavelength-shifting element 250 that includes a plasmonic or dielectric structure 800 that produces emitted light 255 in a concentrated or converging manner may be referred to as a wavelength-shifting element 250 that includes or incorporates a concentrating element 260. In particular embodiments, the emitted-light signal 255 may be substantially insensitive to the angle of incidence Θ of input optical signal 240. As an example and not by way of limitation, for each input beam 240A, 240B, or 240C, the resulting emitted optical signal 255 radiated in the forward direction 360 may have substantially the same wavelength range, optical intensity, and directional character.

Figure 9:
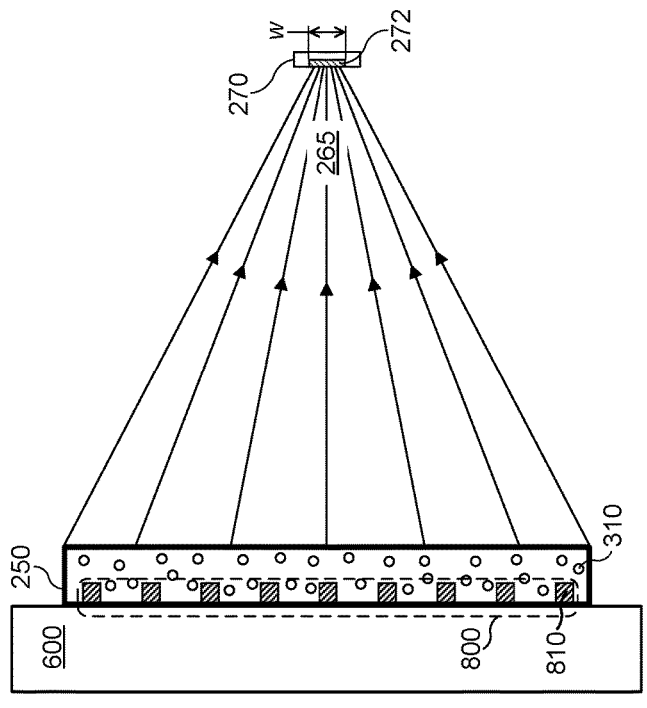
FIG. 9 illustrates an example luminescent detector that includes an example plasmonic or dielectric structure.

FIG. 9 illustrates an example luminescent detector 230 that includes an example plasmonic or dielectric structure 800. In particular embodiments, luminescent detector 230 may include wavelength-shifting element 250 and photodetector 270. As illustrated in FIG. 9, wavelength-shifting element 250 may include wavelength-shifting material 310 and plasmonic or dielectric structure 800. Additionally, wavelength-shifting element 250 may be affixed to substrate 600. As illustrated in FIG. 9, the wavelength-shifting element 250 may be configured to receive input optical signal 240 and, through a fluorescence process, produce an emitted-light signal in the form of concentrated light 265. The emitted-light signal produced by wavelength-shifting element 250 may be directly emitted as concentrated light 265 that converges onto active region 272 of photodetector 270 without requiring a separate focusing element. In the luminescent detector 230 of FIG. 9, the wavelength-shifting element 250 performs both a wavelength-shifting operating as well as a concentrating operation. In particular embodiments, a wavelength-shifting element 250 illustrated in FIG. 9 that includes a plasmonic or dielectric structure 800 that emits light in a concentrated or converging manner may be referred to as a wavelength-shifting element 250 that includes or incorporates a concentrating element 260. As an example and not by way of limitation, the wavelength-shifting element 250 may be referred to as producing an emitted-light signal 255, receiving at least a portion of the emitted-light signal 255, and concentrating the received portion to produce concentrated light 265. In particular embodiments, a plasmonic or dielectric structure 800 may cause the emitted light 255 to be radiated in one or more concentrated or collimated beams, one of the concentrated or collimated beams directed toward photodetector 270. As an example and not by way of limitation, concentrated light 265 directed toward photodetector 270 may include greater than or equal to 40% of the total amount of wavelength-shifted light 255 produced by wavelength-shifting element 250.

In particular embodiments, a luminescent detector 230 as illustrated in FIG. 9 may offer performance advantages similar to those described above with respect to the luminescent detector 230 illustrated in FIG. 7. As an example and not by way of limitation, luminescent detector 230 in FIG. 9 may offer a relatively large effective detector area, a relatively fast response time, a relatively large FOV, and relative insensitivity to wavefront distortion or phase fluctuations of input optical signal 240. Additionally, a luminescent detector 230 that includes a plasmonic or dielectric structure 800 may offer increased optical efficiency by producing light that is emitted in a directional or concentrated manner onto active region 272 of photodetector 270.

Figure 10:
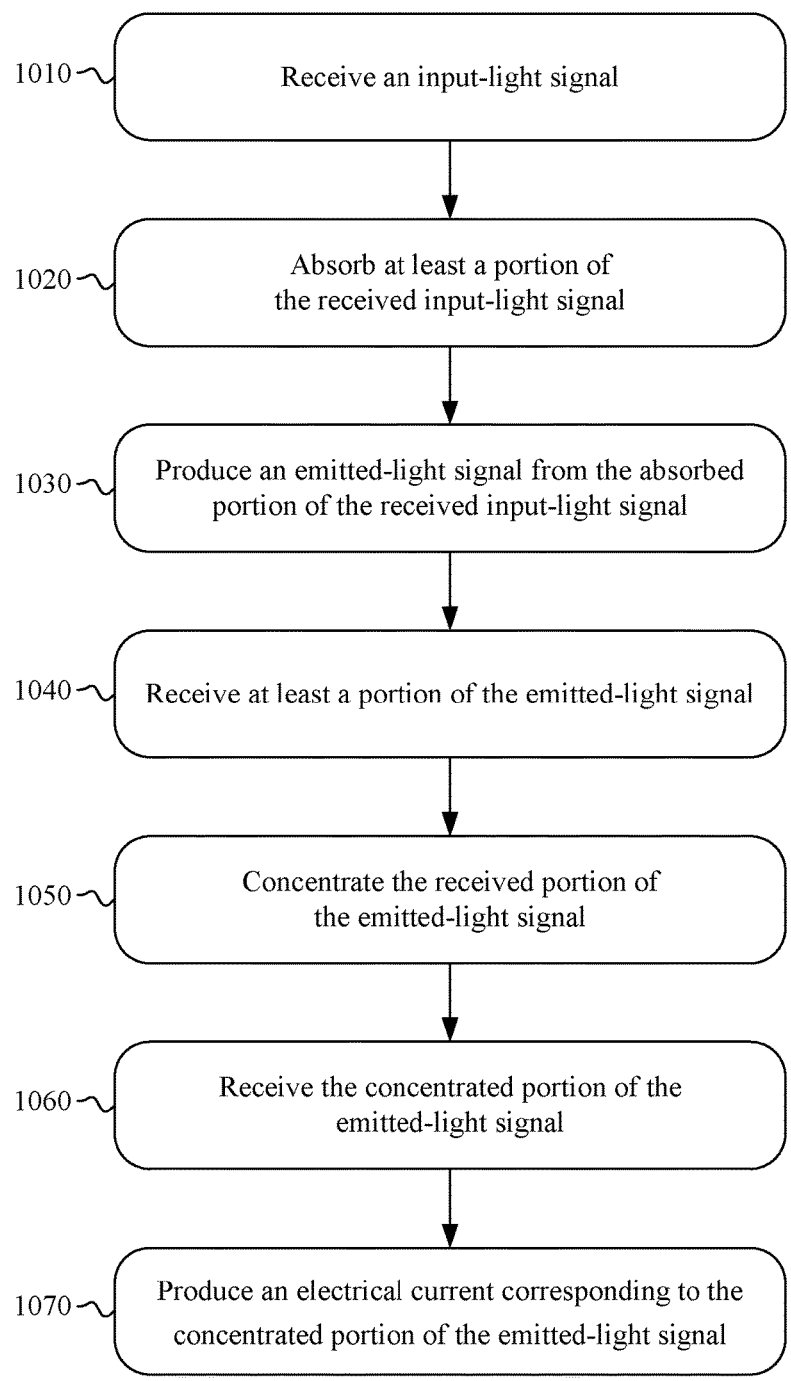
FIG. 10 illustrates an example method for detecting an optical signal using a luminescent detector.

FIG. 10 illustrates an example method for detecting an optical signal using a luminescent detector 230. The method may begin at step 1010, where an input-light signal 240 may be received. As an example and not by way of limitation, a luminescent detector 230 may include a wavelength-shifting element 250 that receives the input-light signal 240. In particular embodiments, the wavelength-shifting element 250 may include a wavelength-shifting material 310. At step 1020, at least a portion of the received input-light signal 240 may be absorbed. As an example and not by way of limitation, the wavelength-shifting material 310 may absorb at least a portion of the received input-light signal 240. At step 1030, an emitted-light signal 255 may be produced from the absorbed portion of the received input-light signal 240. As an example and not by way of limitation, the wavelength-shifting material 310 may produce an emitted-light signal 255 from the absorbed portion of the received input-light signal 240. At step 1040, at least a portion of the emitted-light signal 255 may be received. As an example and not by way of limitation, an optical-concentrating element 260 may receive at least a portion of the emitted-light signal 255. At step 1050, the received portion of the emitted-light signal 255 may be concentrated. As an example and not by way of limitation, an optical-concentrating element 260 may concentrate the received portion of the emitted-light signal 255 onto active region 272 of photodetector 270. As another example and not by way of limitation, the optical-concentrating element 260 may be incorporated into the wavelength-shifting element 250, and the wavelength-shifting element 250 may receive at least a portion of the emitted-light signal 255 and concentrate the received portion as concentrated light 265 onto active region 272 of photodetector 270. At step 1060, the concentrated portion 265 of the emitted-light signal 255 may be received. As an example and not by way of limitation, a photodetector 270 may receive the concentrated portion 265 of the emitted-light signal 255. At step 1070, an electrical current 275 corresponding to the concentrated portion 265 of the emitted-light signal 255 may be produced. As an example and not by way of limitation, a photodetector 270 may produce an electrical current 275 corresponding to the concentrated portion 265 of the emitted-light signal 255. Particular embodiments may repeat one or more steps of the method of FIG. 10, where appropriate. Although this disclosure describes and illustrates particular steps of the method of FIG. 10 as occurring in a particular order, this disclosure contemplates any suitable steps of the method of FIG. 10 occurring in any suitable order. Moreover, although this disclosure describes and illustrates an example method for detecting an optical signal using a luminescent detector 230 including the particular steps of the method of FIG. 10, this disclosure contemplates any suitable method for detecting an optical signal using a luminescent detector 230 including any suitable steps, which may include all, some, or none of the steps of the method of FIG. 10, where appropriate. Furthermore, although this disclosure describes and illustrates particular components, devices, or systems carrying out particular steps of the method of FIG. 10, this disclosure contemplates any suitable combination of any suitable components, devices, or systems carrying out any suitable steps of the method of FIG. 10.

Figure 11:
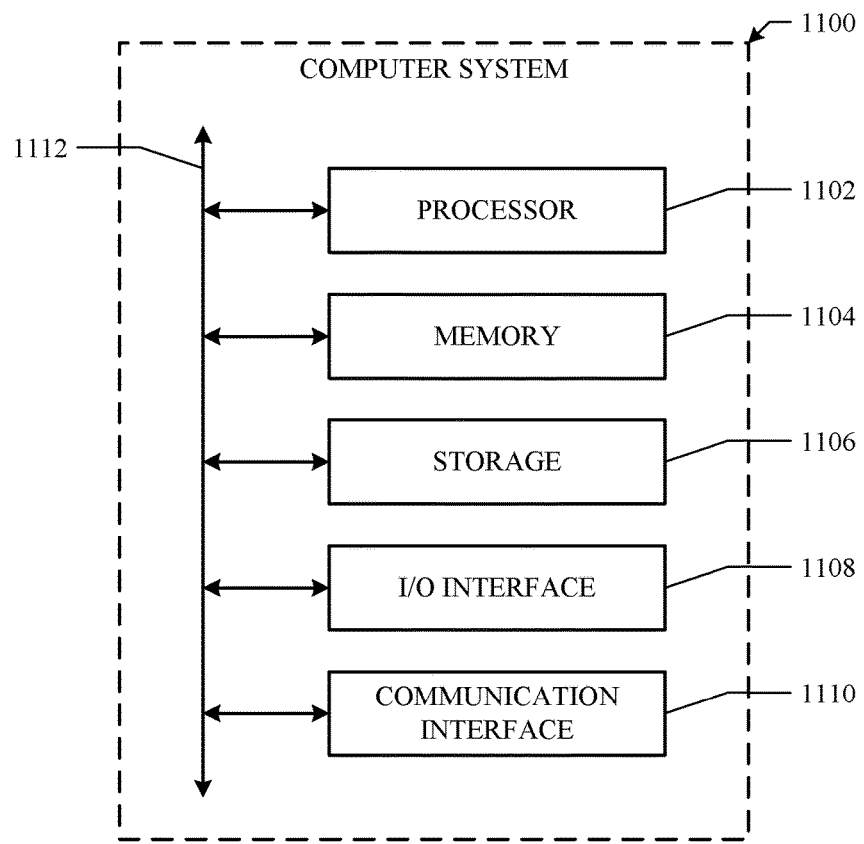
FIG. 11 illustrates an example computer system.

FIG. 11 illustrates an example computer system 1100. In particular embodiments, one or more computer systems 1100 perform one or more steps of one or more methods described or illustrated herein. In particular embodiments, one or more computer systems 1100 provide functionality described or illustrated herein. In particular embodiments, software running on one or more computer systems 1100 performs one or more steps of one or more methods described or illustrated herein or provides functionality described or illustrated herein. Particular embodiments include one or more portions of one or more computer systems 1100. Herein, reference to a computer system may encompass a computing device, and vice versa, where appropriate. Moreover, reference to a computer system may encompass one or more computer systems, where appropriate.

This disclosure contemplates any suitable number of computer systems 1100. This disclosure contemplates computer system 1100 taking any suitable physical form. As example and not by way of limitation, computer system 1100 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, an augmented/virtual reality device, or a combination of two or more of these. Where appropriate, computer system 1100 may include one or more computer systems 1100; be unitary or distributed; span multiple locations; span multiple machines; span multiple data centers; or reside in a cloud, which may include one or more cloud components in one or more networks. Where appropriate, one or more computer systems 1100 may perform without substantial spatial or temporal limitation one or more steps of one or more methods described or illustrated herein. As an example and not by way of limitation, one or more computer systems 1100 may perform in real time or in batch mode one or more steps of one or more methods described or illustrated herein. One or more computer systems 1100 may perform at different times or at different locations one or more steps of one or more methods described or illustrated herein, where appropriate.

In particular embodiments, computer system 1100 includes a processor 1102, memory 1104, storage 1106, an input/output (I/O) interface 1108, a communication interface 1110, and a bus 1112. Although this disclosure describes and illustrates a particular computer system having a particular number of particular components in a particular arrangement, this disclosure contemplates any suitable computer system having any suitable number of any suitable components in any suitable arrangement.

In particular embodiments, processor 1102 includes hardware for executing instructions, such as those making up a computer program. As an example and not by way of limitation, to execute instructions, processor 1102 may retrieve (or fetch) the instructions from an internal register, an internal cache, memory 1104, or storage 1106; decode and execute them; and then write one or more results to an internal register, an internal cache, memory 1104, or storage 1106. In particular embodiments, processor 1102 may include one or more internal caches for data, instructions, or addresses. This disclosure contemplates processor 1102 including any suitable number of any suitable internal caches, where appropriate. As an example and not by way of limitation, processor 1102 may include one or more instruction caches, one or more data caches, and one or more translation lookaside buffers (TLBs). Instructions in the instruction caches may be copies of instructions in memory 1104 or storage 1106, and the instruction caches may speed up retrieval of those instructions by processor 1102. Data in the data caches may be copies of data in memory 1104 or storage 1106 for instructions executing at processor 1102 to operate on; the results of previous instructions executed at processor 1102 for access by subsequent instructions executing at processor 1102 or for writing to memory 1104 or storage 1106; or other suitable data. The data caches may speed up read or write operations by processor 1102. The TLBs may speed up virtual-address translation for processor 1102. In particular embodiments, processor 1102 may include one or more internal registers for data, instructions, or addresses. This disclosure contemplates processor 1102 including any suitable number of any suitable internal registers, where appropriate. Where appropriate, processor 1102 may include one or more arithmetic logic units (ALUs); be a multi-core processor; or include one or more processors 1102. Although this disclosure describes and illustrates a particular processor, this disclosure contemplates any suitable processor.

In particular embodiments, memory 1104 includes main memory for storing instructions for processor 1102 to execute or data for processor 1102 to operate on. As an example and not by way of limitation, computer system 1100 may load instructions from storage 1106 or another source (such as, for example, another computer system 1100) to memory 1104. Processor 1102 may then load the instructions from memory 1104 to an internal register or internal cache. To execute the instructions, processor 1102 may retrieve the instructions from the internal register or internal cache and decode them. During or after execution of the instructions, processor 1102 may write one or more results (which may be intermediate or final results) to the internal register or internal cache. Processor 1102 may then write one or more of those results to memory 1104. In particular embodiments, processor 1102 executes only instructions in one or more internal registers or internal caches or in memory 1104 (as opposed to storage 1106 or elsewhere) and operates only on data in one or more internal registers or internal caches or in memory 1104 (as opposed to storage 1106 or elsewhere). One or more memory buses (which may each include an address bus and a data bus) may couple processor 1102 to memory 1104. Bus 1112 may include one or more memory buses, as described below. In particular embodiments, one or more memory management units (MMUs) reside between processor 1102 and memory 1104 and facilitate accesses to memory 1104 requested by processor 1102. In particular embodiments, memory 1104 includes random access memory (RAM). This RAM may be volatile memory, where appropriate Where appropriate, this RAM may be dynamic RAM (DRAM) or static RAM (SRAM). Moreover, where appropriate, this RAM may be single-ported or multi-ported RAM. This disclosure contemplates any suitable RAM. Memory 1104 may include one or more memories 1104, where appropriate. Although this disclosure describes and illustrates particular memory, this disclosure contemplates any suitable memory.

In particular embodiments, storage 1106 includes mass storage for data or instructions. As an example and not by way of limitation, storage 1106 may include a hard disk drive (HDD), a floppy disk drive, flash memory, an optical disc, a magneto-optical disc, magnetic tape, or a Universal Serial Bus (USB) drive or a combination of two or more of these. Storage 1106 may include removable or non-removable (or fixed) media, where appropriate. Storage 1106 may be internal or external to computer system 1100, where appropriate. In particular embodiments, storage 1106 is non-volatile, solid-state memory. In particular embodiments, storage 1106 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 1106 taking any suitable physical form. Storage 1106 may include one or more storage control units facilitating communication between processor 1102 and storage 1106, where appropriate. Where appropriate, storage 1106 may include one or more storages 1106. Although this disclosure describes and illustrates particular storage, this disclosure contemplates any suitable storage.

In particular embodiments, I/O interface 1108 includes hardware, software, or both, providing one or more interfaces for communication between computer system 1100 and one or more I/O devices. Computer system 1100 may include one or more of these I/O devices, where appropriate. One or more of these I/O devices may enable communication between a person and computer system 1100. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 1108 for them. Where appropriate, I/O interface 1108 may include one or more device or software drivers enabling processor 1102 to drive one or more of these I/O devices. I/O interface 1108 may include one or more I/O interfaces 1108, where appropriate. Although this disclosure describes and illustrates a particular I/O interface, this disclosure contemplates any suitable I/O interface.

In particular embodiments, communication interface 1110 includes hardware, software, or both providing one or more interfaces for communication (such as, for example, packet-based communication) between computer system 1100 and one or more other computer systems 1100 or one or more networks. As an example and not by way of limitation, communication interface 1110 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 1110 for it. As an example and not by way of limitation, computer system 1100 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 1100 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 1100 may include any suitable communication interface 1110 for any of these networks, where appropriate. Communication interface 1110 may include one or more communication interfaces 1110, where appropriate. Although this disclosure describes and illustrates a particular communication interface, this disclosure contemplates any suitable communication interface.

In particular embodiments, bus 1112 includes hardware, software, or both coupling components of computer system 1100 to each other. As an example and not by way of limitation, bus 1112 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 1112 may include one or more buses 1112, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

What is claimed is:

1. An apparatus comprising:
a wavelength-shifting element configured to receive an input-light signal, wherein the wavelength-shifting element comprises a wavelength-shifting material configured to:
absorb at least a portion of the received input-light signal; and
produce an emitted-light signal from the absorbed portion of the received input-light signal;
a plasmonic grating comprising a plurality of plasmonic-structure elements, wherein each plasmonic-structure element extends perpendicular to a side of the wavelength-shifting element, the plasmonic grating configured to:
receive at least a portion of the emitted-light signal; and
concentrate the received portion of the emitted-light signal onto a photodetector; and
the photodetector configured to:
receive the concentrated portion of the emitted-light signal; and
produce an electrical current corresponding to the concentrated portion of the emitted-light signal.

2. The apparatus of claim 1, wherein the input-light signal is a free-space optical-communication signal sent from an optical transmitter.

3. The apparatus of claim 1, wherein the wavelength-shifting material has an upper-state lifetime of less than or equal to 10 nanoseconds.

4. The apparatus of claim 1, wherein the wavelength-shifting element further comprises a substantially transparent encapsulant material, wherein the wavelength-shifting material is contained within the encapsulant material.

5. The apparatus of claim 4, wherein an upper-state lifetime of the wavelength-shifting material is reduced due to properties of the encapsulant material.

6. The apparatus of claim 4, wherein a quantum efficiency of the wavelength-shifting material is increased due to properties of the encapsulant material.

7. The apparatus of claim 1, wherein the wavelength-shifting element has a thickness of approximately 0.05 μm to approximately 1 mm.

8. The apparatus of claim 1, wherein the wavelength-shifting material comprises a fluorescent-dye material or a plurality of quantum dots.

9. The apparatus of claim 1, wherein the wavelength-shifting material is a non-isotropic emitter that preferentially radiates the emitted-light signal in a forward direction or a backward direction.

10. The apparatus of claim 1, wherein the wavelength-shifting material of the wavelength-shifting element absorbs greater than or equal to 70% of the input-light signal.

11. The apparatus of claim 1, wherein the absorbed portion of the received input-light signal comprises visible or near-infrared light and the emitted-light signal has a wavelength range that is longer than a wavelength range of the absorbed portion of the received input-light signal.

12. The apparatus of claim 1, wherein:
the wavelength-shifting element comprises an input aperture configured to receive the input-light signal, wherein the input aperture has a diameter or width of greater than or equal to 1 cm; and
the photodetector has an active element with a diameter or width of less than or equal to 1 mm.

13. The apparatus of claim 1, wherein:
the wavelength-shifting element comprises an input aperture configured to receive the input-light signal, wherein the input aperture has a diameter or width of greater than or equal to 1 mm; and
the photodetector has an active element with a diameter or width of less than or equal to 20 micrometers.

14. The apparatus of claim 1, wherein the portion of the emitted-light signal received by the plasmonic grating comprises greater than or equal to 25% of the emitted-light signal.

15. The apparatus of claim 1, wherein the plasmonic grating is incorporated into the wavelength-shifting element.

16. The apparatus of claim 1, wherein the plasmonic grating is configured to cause the emitted-light signal to be radiated in one or more collimated beams.

17. A method comprising:
receiving an input-light signal;
absorbing at least a portion of the received input-light signal;
producing an emitted-light signal from the absorbed portion of the received input-light signal;
receiving at least a portion of the emitted-light signal;
concentrating the received portion of the emitted-light signal by using a plasmonic grating, the plasmonic grating comprising a plurality of plasmonic-structure elements, wherein each plasmonic-structure element extends perpendicular to a side of a wavelength shifting element;
receiving the concentrated portion of the emitted-light signal; and
producing an electrical current corresponding to the concentrated portion of the emitted-light signal.

18. An apparatus comprising:
means for receiving an input-light signal;
means for absorbing at least a portion of the received input-light signal;
means producing an emitted-light signal from the absorbed portion of the received input-light signal;
means for receiving at least a portion of the emitted-light signal;
means for concentrating the received portion of the emitted-light signal comprising a plasmonic grating, the plasmonic grating comprising a plurality of plasmonic-structure elements, wherein each plasmonic-structure element extends perpendicular to a side of a wavelength shifting element;
means for receiving the concentrated portion of the emitted-light signal; and
means for producing an electrical current corresponding to the concentrated portion of the emitted-light signal.

19. The apparatus of claim 1, wherein the plurality of plasmonic structure elements are affixed to a side of the wavelength-shifting element that is opposite to a side that absorbs the emitted-light signal.

20. The apparatus of claim 1, wherein receiving at least a portion of the emitted-light signal comprises coupling one or more photons of the emitted light signal to one or more of the plasmonic-structure elements to generate one or more plasma oscillations.

\* \* \* \* \*